(12) United States Patent
Feinberg et al.

(10) Patent No.: US 11,926,844 B2
(45) Date of Patent: Mar. 12, 2024

(54) THREE-DIMENSIONAL MICROTISSUES WITH INTEGRATED MECHANICAL LOADING

(71) Applicant: Carnegie Mellon University, Pittsburgh, PA (US)

(72) Inventors: Adam Feinberg, Pittsburgh, PA (US); Rebecca Duffy, Pittsburgh, PA (US); Jacqueline Wittmer, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 812 days.

(21) Appl. No.: 16/638,544

(22) PCT Filed: Aug. 8, 2018

(86) PCT No.: PCT/US2018/000165
§ 371 (c)(1),
(2) Date: Feb. 12, 2020

(87) PCT Pub. No.: WO2019/035898
PCT Pub. Date: Feb. 21, 2019

(65) Prior Publication Data
US 2020/0216801 A1 Jul. 9, 2020

Related U.S. Application Data

(60) Provisional application No. 62/605,475, filed on Aug. 15, 2017.

(51) Int. Cl.
| | |
|---|---|
| C12N 5/00 | (2006.01) |
| C12M 1/00 | (2006.01) |
| C12M 1/32 | (2006.01) |
| C12N 5/071 | (2010.01) |
| G01N 3/06 | (2006.01) |
| G01N 3/20 | (2006.01) |
| G01N 33/483 | (2006.01) |
| G01N 33/50 | (2006.01) |

(52) U.S. Cl.
CPC ........... *C12N 5/0062* (2013.01); *C12M 23/12* (2013.01); *C12M 23/26* (2013.01); *C12N 5/0697* (2013.01); *G01N 3/066* (2013.01); *G01N 3/20* (2013.01); *G01N 33/4833* (2013.01); *G01N 33/5008* (2013.01); *C12N 2513/00* (2013.01); *G01N 2500/00* (2013.01)

(58) Field of Classification Search
None
See application file for complete search history.

(56) References Cited

U.S. PATENT DOCUMENTS

| | | | |
|---|---|---|---|
| 4,789,601 A | 12/1988 | Banes | |
| 5,153,136 A | 10/1992 | Vadenburgh | |
| 6,057,150 A | 5/2000 | Lee et al. | |
| 6,107,081 A * | 8/2000 | Feeback | ........... G01N 3/08 435/284.1 |
| 2005/0244961 A1 | 11/2005 | Short et al. | |
| 2010/0190249 A1 | 7/2010 | Kruse et al. | |
| 2011/0165671 A1 | 7/2011 | Halter et al. | |
| 2014/0094388 A1* | 4/2014 | Wakatsuki | ........... C12N 5/0697 435/6.13 |
| 2016/0152946 A1 | 6/2016 | Choi et al. | |

FOREIGN PATENT DOCUMENTS

| | | | |
|---|---|---|---|
| WO | WO 2016/036532 | 3/2016 | |
| WO | WO-2016183143 A1 * | 11/2016 | ............. A61K 35/34 |

OTHER PUBLICATIONS

Serrao et al. "Myocyte-depleted engineered cardiac tissues support therapeutic potential of mesenchymal stem cells." Tissue Engineering Part A 18.13-14 (2012): 1322-1333. (Year: 2012).*
Burridge et al. "Chemically defined generation of human cardiomyocytes," Nat. Methods, 11:855-60, Jun. 2014.
Burridge et al., "Human induced pluripotent stem cell-derived cardiomyocytes recapitulate the predilection of breast cancer patients to doxorubicin-induced cardiotoxicity," Nature Med., 22:547-56, Apr. 2016.
Chan et al., "Fabrication and characterization of optogenetic, multistrip cardiac muscles," Lab Chip, 15(10):2258-68, May 2015.
Chen et al., "Phospholamban as a Crucial Determinant of the Inotropic Response of Human Pluripotent Stem Cell-Derived Ventricular Cardiomyocytes and Engineered 3-Dimensional Tissue Constructs," Circulation-Arrhythmia and Electrophysiology, 8,(1):193-202, Dec. 2014.
Eder et al., "Human engineered heart tissue as a model system for drug testing," Adv. Drug Delivery Rev., 96,:214-24, Jan. 2016.
Eschenhagen et al., "Three-dimensional reconstitution of embryonic cardiomyocytes in a collagen matrix: a new heart muscle model system," Faseb J., 11(8):683-94, Jul. 1997.
Feinberg et al., "Muscular Thin Films for Building Actuators and Powering Devices," Science, 317(5843):1366-70, Sep. 2007.
Galie et al., "Mechanically Stimulated Contraction of Engineered Cardiac Constructs Using a Microcantilever," IEEE Trans. Biomed. Eng., 62(2):438-42, Feb. 2015.
Hansen et al., "Development of a Drug Screening Platform Based on Engineered Heart Tissue," Cir. Res., 107:35-44, 2010.
Kijlstra et al., "Integrated Analysis of Contractile Kinetics, Force Generation, and Electrical Activity in Single Human Stem Cell-Derived Cardiomyocytes," Stem Cell Rep., 5(6):1226-38, Dec. 2015.

(Continued)

*Primary Examiner* — Emily A Cordas
(74) *Attorney, Agent, or Firm* — Fish & Richardson P.C.

(57) ABSTRACT

This document describes systems and methods for integrated mechanical loading of tissue. The system includes a three-dimensional tissue comprising organic material. The system includes a strip of bendable material. The strip includes a first region proximate to a first end of the strip coupled to the tissue. The strip includes a second region near a second end of the strip for coupled to the tissue, the second end being opposite the first end, wherein the tissue exerts a force on the strip to bend the strip, the force caused by contraction of the tissue, and wherein the strip exerts a stress on the tissue.

18 Claims, 24 Drawing Sheets

(56) References Cited

OTHER PUBLICATIONS

Lian et al., "Directed cardiomyocyte differentiation from human pluripotent stem cells by modulating Wnt/β-catenin signaling under fully defined condition,". Nat. Protoc., 8:162-75, Dec. 2012.

Liau et al., "Pluripotent stem cell-derived cardiac tissue patch with advanced structure and function," Biomaterials, 32(35): 9180-7, Dec. 2011.

Madden et al., "Bioengineered human myobundles mimic clinical responses of skeletal muscle to drugs" eLife, 4:e0488, Jan. 2015.

Mewes and Ravens, "L-type Calcium Currents of Human Myocytes from Ventricle of Non-failing and Failing Hearts and from Atrium," J. Mole. Cell. Cardiol., 6(10):1307-20, Oct. 1994.

PCT International Search Report and Written Opinion in International Appln. No. International application No. PCT/US2018/000165, dated Dec. 14, 2018, 10 pages.

Ribeiro et al., "Functional maturation of human pluripotent stem cell derived cardiomyocytes in vitro—Correlation between contraction force and electrophysiology," Biomaterials 51:138-50, May 2015.

Saini et al., "3D Cardiac Microtissues Encapsulated with the CoCulture of Cardiomyocytes and Cardiac Fibroblasts," Adv. Healthcare Materials, 4(13):1961-71, Jun. 2015.

Schaaf et al., "Human Engineered Heart Tissue as a Versatile Tool in Basic Research and Preclinical Toxicology," PLoS One, 6(10):e26397, Oct. 2011.

Sheng et al.,"Human Pluripotent Stem Cell-Derived Cardiomyocytes: Response to TTX and Lidocain Reveals Strong Cell to Cell Variability," PloS One, 7(9):e45963, Sep. 2012.

Sun et al., "Optimizing the structure and contractility of engineered skeletal muscle thin films,".Acta Biomaterialia, 9(8):7885-94, Aug. 2013.

Thavandiran et al., "Design and formulation of functional pluripotent stem cell-derived cardiac microtissues," Proc. Natl. Acad. Sci. USA., 110(49):e4698-707, Dec. 2013.

Van Spreeuwel al., "The influence of matrix (an)isotropy on cardiomyocyte contraction in engineered cardiac microtissues," Integrative Biol., 6(4):422-9, Apr. 2014.

Xiao et al., "Microfabricated perfusable cardiac biowire: a platform that mimics native cardiac bundle," Lab Chip, 14(5):869-82, Mar. 2014.

Zhang et al., "Tissue-engineered cardiac patch for advanced functional maturation of human ESC-derived cardiomyocyte,". Biomaterials, 34(23):5813-20, Jul. 2013.

PCT International Preliminary Report on Patentability in International Appln. No. PCT/US2018/000165, dated Feb. 27, 2020, 7 pages.

\* cited by examiner

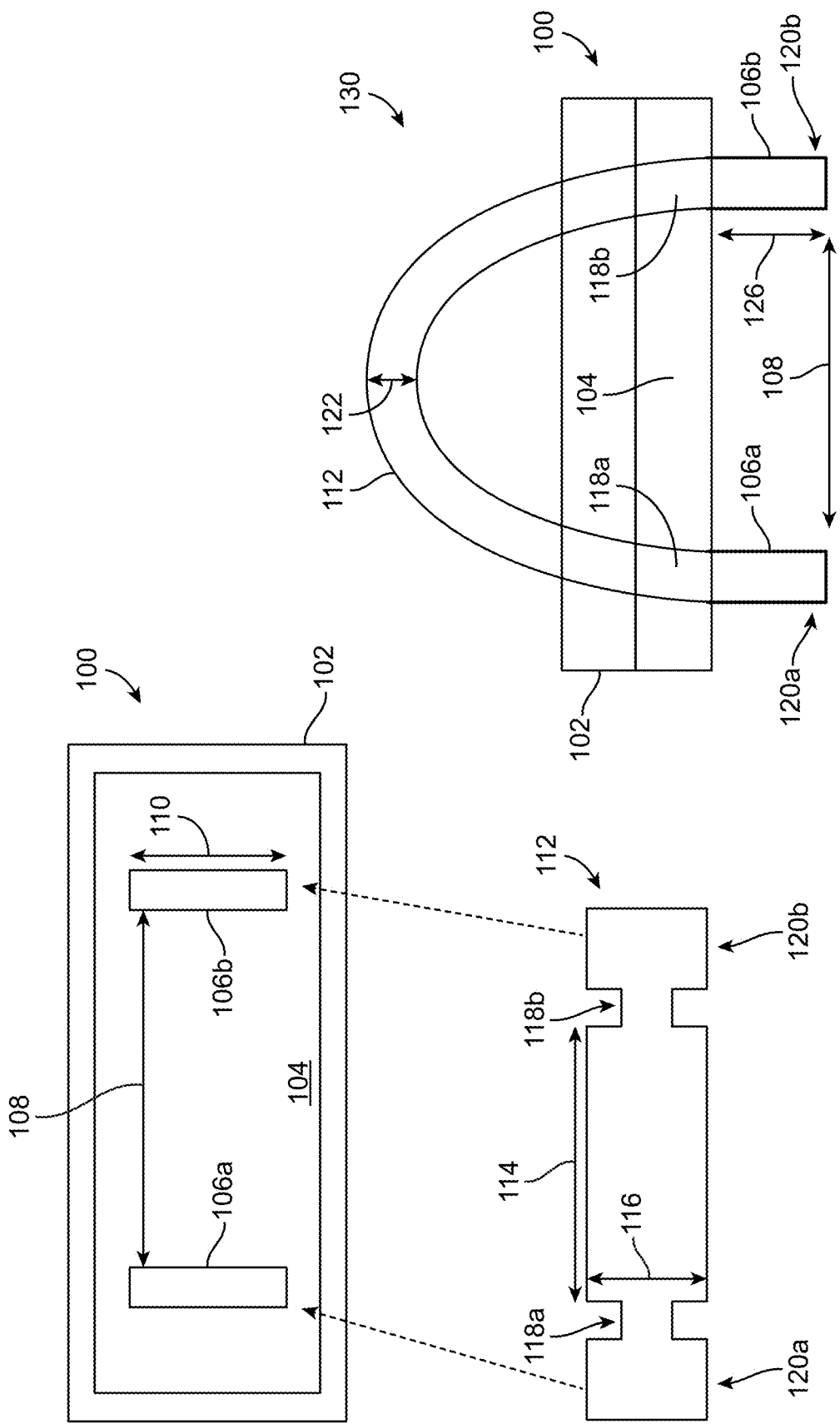

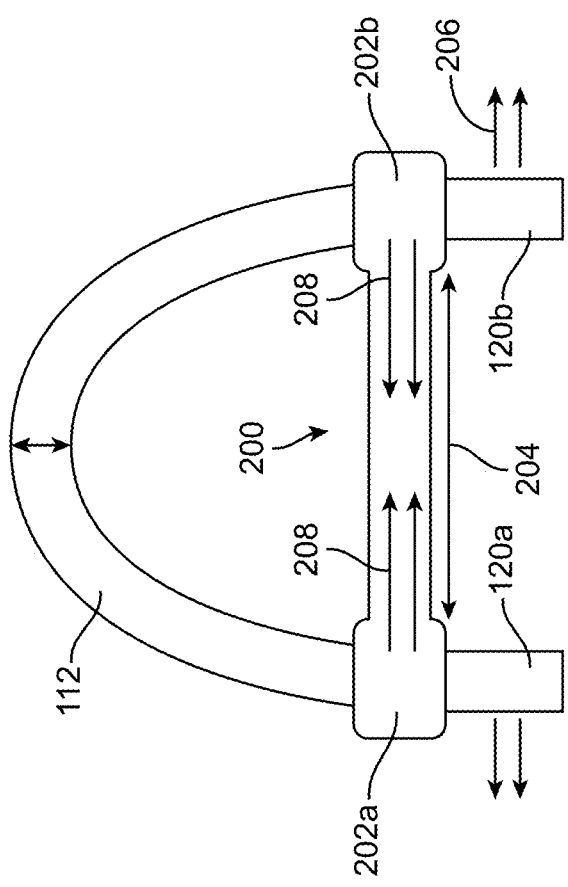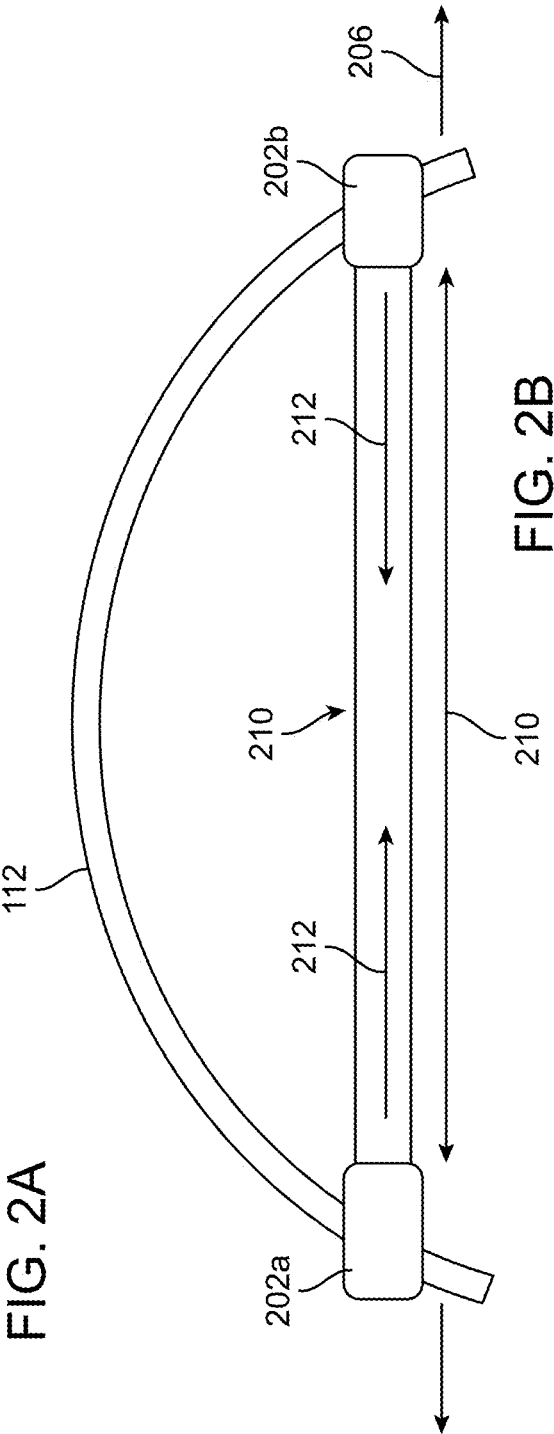

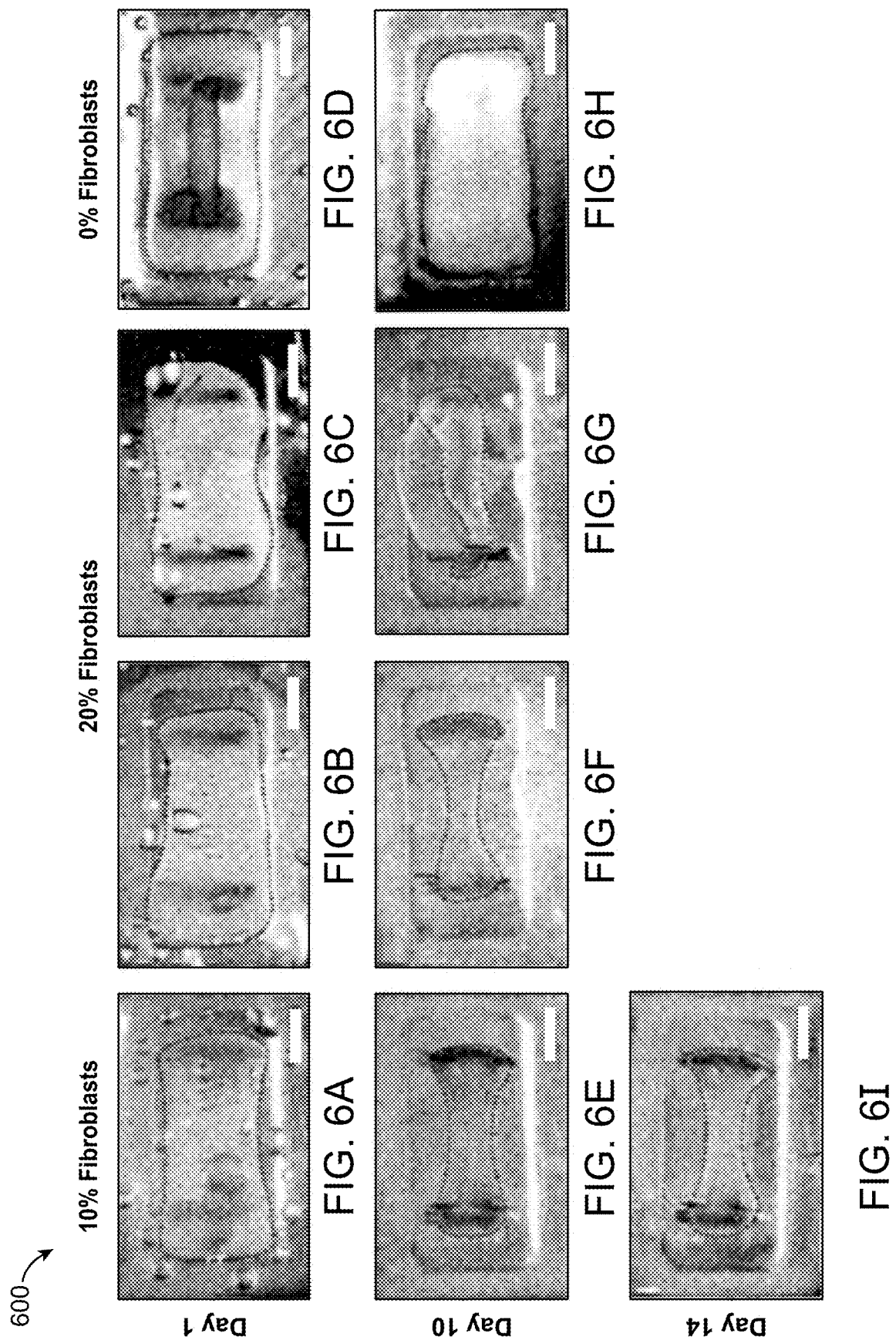

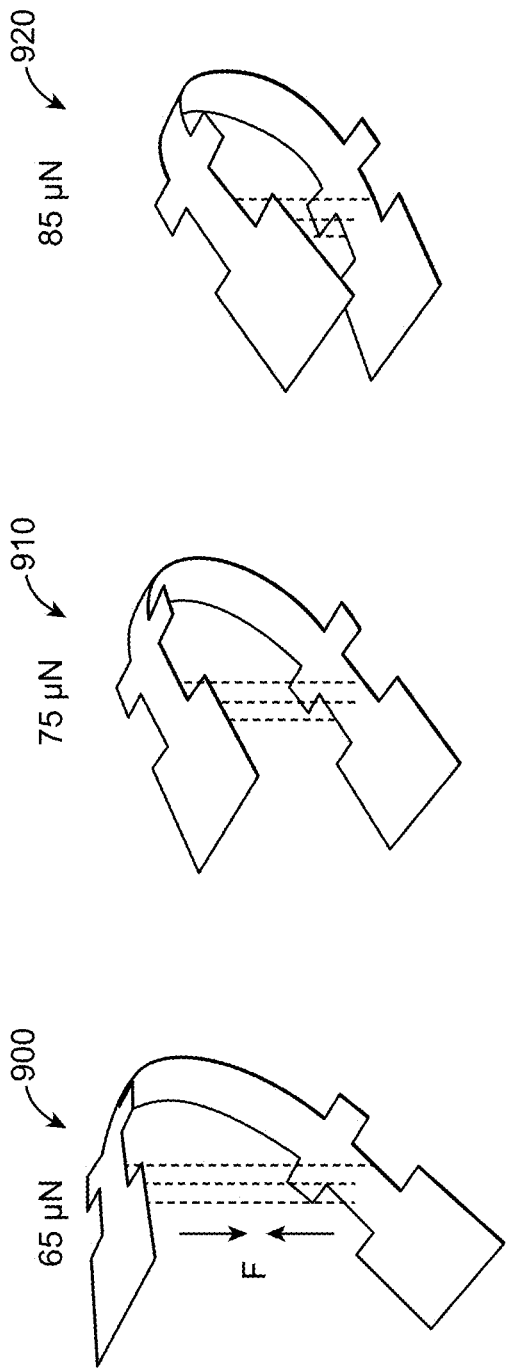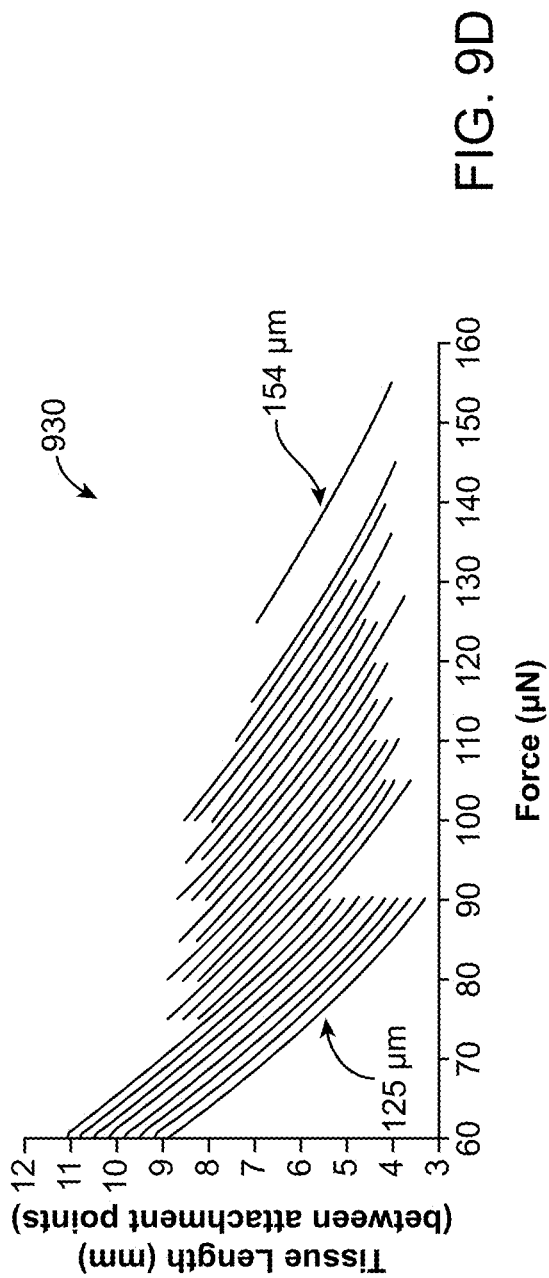
FIG. 9A FIG. 9B FIG. 9C FIG. 9D

Day 14 - 10% FB - Regular Beating

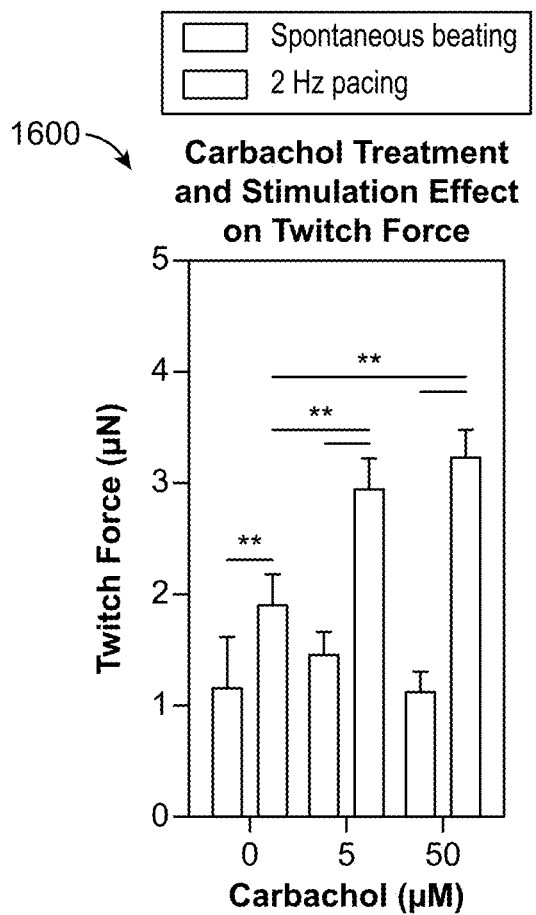
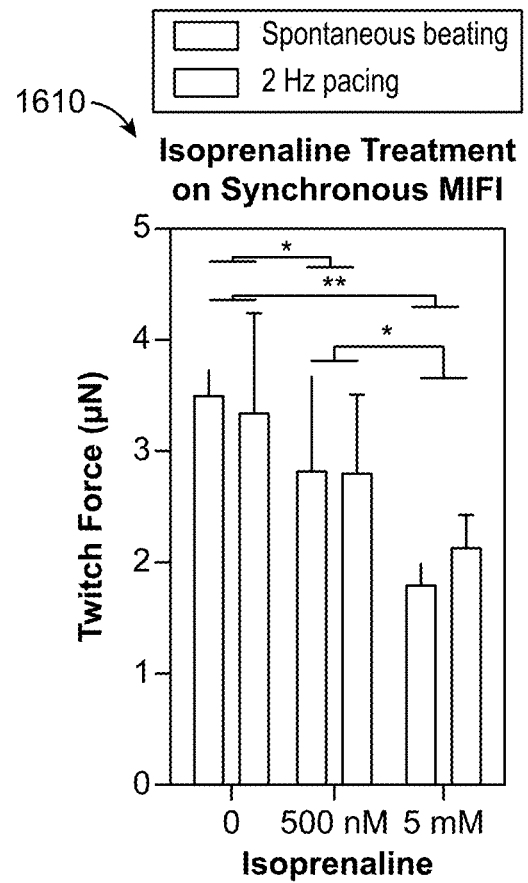
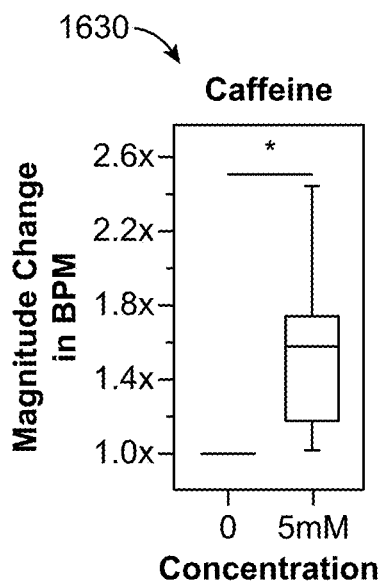
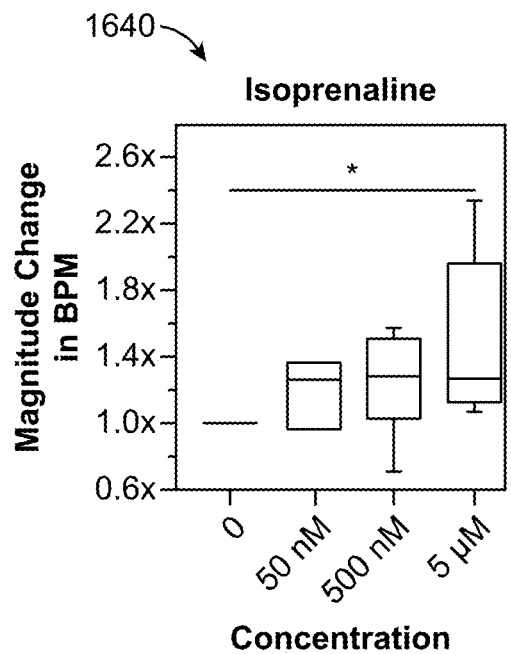
FIG. 16

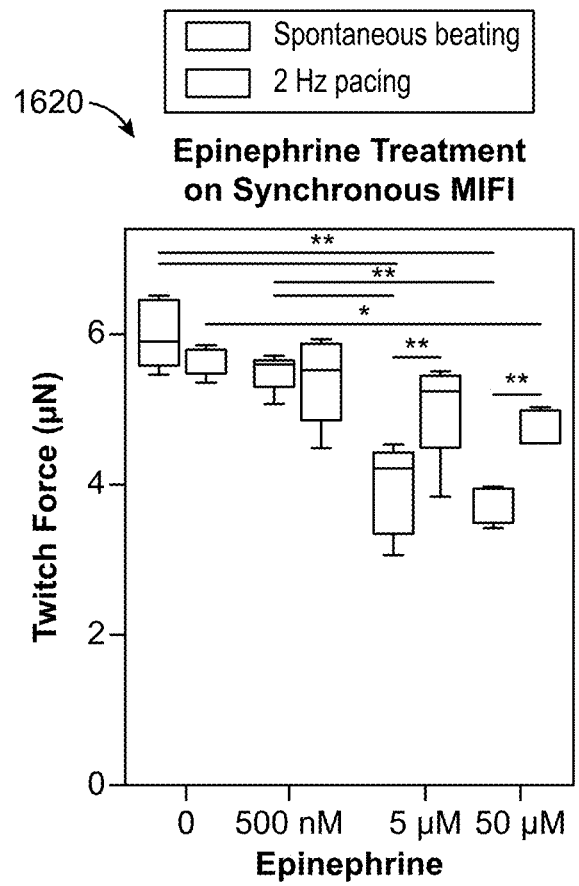
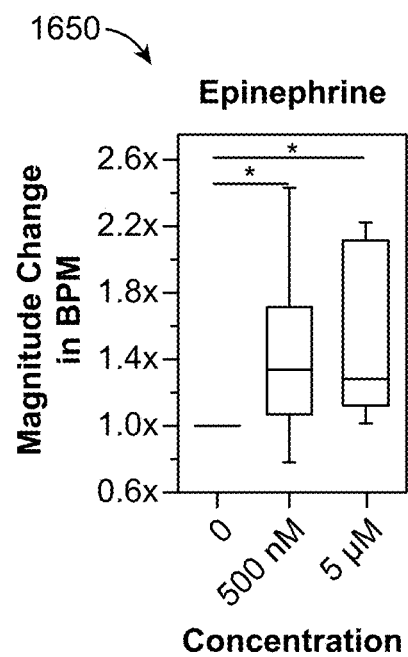
FIG. 16 (Cont.)

THREE-DIMENSIONAL MICROTISSUES WITH INTEGRATED MECHANICAL LOADING

CLAIM OF PRIORITY

This application under 35 U.S.C. § 371 is a National Stage Application of PCT/US2018/000165, filed Aug. 15, 2018, which, in turn, claims the benefit of priority under 35 U.S.C. § 119(e) to U.S. Patent Application Ser. No. 62/605,475, filed on Aug. 15, 2017, the entire contents of each of which are hereby incorporated by reference.

STATEMENT OF GOVERNMENT RIGHTS

This invention was made with government support under HL117750 awarded by National Institute of Health. The government has certain rights in the invention.

TECHNICAL FIELD

This document relates to tissue generation.

BACKGROUND

Engineered three-dimensional (3D) in vitro models of functional human tissues have applications as physiologically relevant but more economical platforms for pharmacological testing (compared to human and animal trials), disease models and disease modeling (e.g., genetically tailored disease modeling), and building blocks to engineer functional organ replacements in the future. Animal models do not typically accurately predict the response pharmacological stimuli will have on human patients. 2D in vitro cultures of human cells do not accurately predict the response pharmacological stimuli will have on human patients. For example, a process for engineering in vitro 3D cardiac muscle from human stem cell derived cardiomyocytes (CMs) instead of animal CMs enables engineered cardiac muscle that is physiologically more similar to adult human heart muscle. Further, engineered cardiac heart muscle that is representative of human physiology would fill a critical void between animal models and human clinical trials. However, human adult CMs are terminally differentiated and cannot be expanded in vitro. The only robust source of new human CMs are from pluripotent stem cells including either embryonic stem cells (ESCs) or induced pluripotent stem cells (iPSCs). In fact, much in vitro understanding of cardiac function has focused on individual CM behavior. Specifically, focus has been placed on differentiating more functionally mature CMs from ESCs or iPSCs. Additional studies have examined individual pluripotent stem cell-derived CM response to different pharmacological stimuli in terms of electrical activity, force generation, and gene expression. The challenge with iPSC and ESC-derived CMs is that they are often more functionally immature than in vivo adult CMs. Specifically, these CMs are often round rather than spread and classically rod-shaped, exhibit disordered sarcomere organization, and have smaller membrane capacitance than adult CMs. Determining how to differentiate more functionally mature CMs from stem cells is key to engineering functional cardiac tissues, but a necessary next step is developing more complex, physiologically representative, 3D microtissues (tissues) by building on these individual CM studies.

Furthermore, current preclinical research for treatment and disease modeling is often performed on animals or 2D cell cultures. Muscular Thin Films (MTFs) and cardiac tissues are exposed to a static load that may not accurately model diseases in which load on the heart muscle increases and are isometrically constrained.

SUMMARY

This document describes methods and systems for generating 3D tissues that are integrated with mechanical loading. The tissues generated are representative of human physiology and we describe and example that includes differentiated, functionally mature muscle tissues such as CMs exhibiting striations. Tissues are fabricated with an attached strip of material (e.g., a PDMS strip), which can be used to load the tissue and measure tissue contractile force. The material strip has known mechanical properties, and the strip bending is quantified to determine tissue contractile force of the generated tissue. For example, strip bending is measured by taking one or more images of the strip and tissue, processing the images to determine the geometry of the strip with respect to the tissue, and determining the strip contractile force based on the determined geometry of the strip. The tissues are referred to as mircrotissues (µtissues) and/or 3D tissues because the tissues have a length, width and thickness and are not grown as two-dimensional cell cultures on cover slips or films. The tissue can include muscle tissues (cardio, skeletal, etc.), tendons, ligaments, cartilage, skin and so forth.

In some implementations, strip is bent in to a semi-circle shape and the tissue is formed across the ends, in a horse shoe like configuration. The tissue contractile force is determined by measuring the radius of curvature of the strip and its length with respect to the tissue. Measurements in tissue length and force are plotted over time. A twitch force is determined based on the difference between an average systolic force and an average diastolic force of the tissue. Thus, because the strip can be viewed with a standard microscope, this process includes a non-invasive method of determining tissue contractile force of the generated tissue, in comparison to the laborious process of connecting the microtissue to a mechanical force probe.

The advantages of the tissues and methods for generating herein are described below. Cells grown in vitro in 2D are by definition adhered to a cover slip or other substrate. This adhesion to a substrate limits the ability of the cells to recapitulate the structure and function of real 3D tissues in the human body. Higher cell-substrate interactions (such as those in 2D and similar deformable 2D systems such as muscular thin films) are unsuitable for modeling cardiac disease phenotypes driven predominantly by defects in cell-cell or cell-matrix interactions. While 2D cells are isometrically constrained because they are adhered to rigid substrate that they cannot deform. Rather, the 3D tissues described below are not constrained by an underlying substrate and therefore free to contract and shorten in length in response to a stimuli, producing a contractile stress that works against the mechanical loading of the strip. Tissues are fabricated with an attached strip of bendable material (e.g., PDMS material, a thermoplastic such as Teflon™ film, polycarbonate film, etc.), whereby strip bending is quantified to determine tissue contractile force. The parameters of the strips, which include length, elastic modulus, width, thickness, and so forth, are tuned to particular values to create a defined mechanical load. This parameter space is useful for generating many variations of the tissue and the mechanical loading for high-throughput assay (HTA) processes. Specifically, the parameters are altered to change the bending stiffness of the strip, making each well of an assay plate unique, if needed. Such applications include modeling cardiac diseases, which often are caused by of produce an altered loading of the heart. In a specific example, a PDMS strip has tunable bending stiffness, in which the PDMS strip parameters are changed to alter the bending stiffness that the cardiac tissue must contract against. This enables modulation of the load a cardiac tissue experiences. The load can be tuned to be on the order of ~1 kPa to 10,000 kPa.

Because the 3D tissue attached to the strip is not isometrically constrained, this allows the tissue to undergo large strains of about 10-20%, which is more reminiscent of the adult myocardium. As the cardiac tissue contracts it bends the PDMS strip. As stated above, the curvature of the strip is measured in a noninvasive manner (e.g., by brightfield microscopy and image processing) to quantity tissue contractile force without disturbing the tissue contraction. It is also possible to modulate between constrained and unconstrained condition, which enables tissue development where the tissue can contract in excess of 40% of an initial length of the tissue. This tissue thus closely resembles adult myocardium (or other such tissue that is generated) that can be interrogated to acquire data such as twitch rate, contraction, structure, histology, force generation, electrophysiology, conduction velocity, gene expression, protein expression, or other data acquired from such assays performed on tissues.

The system includes a strip of bendable material, the strip including: a first region in proximity to a first end of the strip for coupling to a tissue including organic material; and a second region in proximity to a second end of the strip for coupling to the tissue, the second end being opposite the first end, where the strip is configured to bend to align the first region with the second region; and a well for generating the tissue, the well including: a region for generating the tissue from a cell culture; a first slit configured to receive the first end of the strip and expose the first region of the strip to the tissue generation region; and a second slit configured to receive the second end of the strip and expose the second region of the strip to the region of the well; where the first slit is aligned with the second slit to align the first region of the strip and the second region of the strip in the region to enable the tissue to couple to the first region of the strip and to couple to the second region of the strip during generation of the tissue.

In some implementations, the well is configured to reduce a stress exerted by the strip from on the tissue during generation of the tissue relative to a maximum stress that the strip is configured to exert on the tissue; and where the strip is configured to exert the maximum stress on the tissue when the strip and the tissue are removed from the well. In some implementations, the strip is configured to provide a stress of up to approximately 10,000 kPa on the tissue when the strip and the tissue are removed from the well.

In some implementations, a magnitude of the stress exerted on the tissue by the strip is a function of one or more tuned parameters of the strip, the parameters including a length of the strip, a width of the strip, a thickness of the strip, an elastic modulus of the strip, and a shape of the strip. In some implementations, the tissue is configured for contracting between approximately 10%-40% of an initial length of the tissue.

In some implementations, a cell suspension of the well comprises an approximate mixture of either 0.5 to 10 mg/mL Collagen Type I or fibrin, 20% Matrigel®, 10% 10× phosphate buffered saline, and either $18.75 \times 10^6$ cells/mL for cardiomyocytes or $15 \times 10^6$ cells/mL for myoblasts. A cell suspension of the well comprises a concentration of between approximately $10-100 \times 10^6$ cells/mL and fibroblasts including approximately 10-20% of a total cell count. In some implementations, cells of the cell suspension comprise one of smooth muscle cells, skin cells, ligament cells, and tendon cells.

In some implementations, the well is a part of a multi-well plate. In some implementations, at least one well of the multi-well plate corresponds to a respective strip having particular parameters, and where at least one strip and well of the multi-well plate represent a loading value of a parameter space representing loading values for the tissue.

In some implementations, the particular parameters of the strip comprise an elastic modulus parameter, a thickness parameter, a width parameter, and a length parameter. In some implementations, the strip comprises one of polydimethylsiloxane (PDMS), Teflon™ film, or a polycarbonate film. In some implementations, each of the first region and the second region of the strip has a narrower width than a width of a portion of the strip between the first region and the second region.

In some implementations, the tissue comprises one of a cardiac tissue, skeletal tissue, smooth muscle tissue, skin tissue, cartilage, tendon, and ligament. In some implementations, the tissue forms striations in response to a stress exerted on the tissue by the strip. In some implementations, cells within the tissue align in response to a stress exerted on the tissue by the strip. The tissue is configured to undergo a strain of up to 80% by the strip when the strip and tissue are removed from the well.

In some implementations, a process for generating a tissue with an integrated load includes generating a tissue that is affixed to a strip of bendable material, the tissue being affixed to a first end and a second, opposite end of the strip. The process includes causing the tissue be in a contracted state and exert a stress on the strip to bend the strip. The process includes measuring a curvature of the strip when the tissue is in the contracted state and exerting the stress on the strip. The process includes calculating the stress exerted on the strip by the tissue, the stress being a function of the curvature of the strip and one or more parameters of the strip, the one or more parameters each having a value that is pre-determined.

In some implementations, the process includes tuning an action potential of the tissue by adjusting the one or more parameters of the strip; applying a voltage to the tissue; and responsive to application of the voltage, measuring the action potential of the tissue using calcium or voltage imaging. In some implementations, the process includes measuring an organization of cell cytoskeletal components. In some implementations, the process includes measuring an epigenetic change in the tissue. In some implementations, the process includes measuring a gene or protein expression of the tissue. In some implementations, the process includes measuring a gene or protein expression of the tissue.

In some implementations, the process includes controlling, during the generating of the tissue, a density of the tissue by adjusting a concentration of a cell culture in a hydrogel mixture. In some implementations, the hydrogel mixture includes at least one of fibrinogen, Matrigel®, a hyaluronic acid hydrogel, or a synthetic hydrogel.

In some implementations, at least one of the one or more parameters comprise a thickness of the strip, a width of the strip, an elastic modulus of the strip and a length of the strip. The process further includes selecting the value of the one or more parameters to tune a magnitude of a stress exerted on the tissue by the strip to a particular value.

In some implementations, the process includes adding a compound to the tissue so that the tissue absorbs the compound and causing the tissue be in a contracted state and exert a stress on the strip to bend the strip once the compound is absorbed by the tissue. The compound comprises a drug candidate. In some implementations, the process includes adding a compound to the tissue so that the tissue absorbs the compound; and causing the tissue be in a relaxed state once the compound is absorbed by the tissue so that the strip extends the tissue.

In some implementations, a process for generating a tissue includes adding, to a well, a cell suspension mixture, the well including a strip of bendable material, where the strip of bendable material is inserted into the well at a first end and at a second end opposite the first end so that the strip is curved; generating, from the cell suspension mixture, a tissue that is affixed to the first end of the strip and the second end of the strip; and removing the strip from the well, where the strip is configured to exert a stress on the tissue after the strip is removed from the well, and where the strip exerts a reduced stress on the tissue before the strip is removed from the well relative to an increased stress on the tissue after the strip is removed from the well.

In some implementations, the system includes a three dimensional tissue including organic material; and a strip of bendable material, the strip including: a first region proximate to a first end of the strip coupled to the tissue; a second region near a second end of the strip for coupled to the tissue, the second end being opposite the first end, where the tissue exerts a force on the strip to bend the strip, the force caused by contraction of the tissue, and where the strip exerts a stress on the tissue.

In some implementations, the tissue is isometrically unconstrained. In some implementations, the tissue is configured to contract by at least 10% an initial length of the tissue. In some implementations, the tissue is configured to contract by at least 20% an initial length of the tissue.

In some implementations, a process includes selecting one or more parameters of a strip to tune a loading value of the strip that the strip is configured to exert; generating a tissue that is integrated with the strip that provides the loading value on the tissue; adding a compound to the tissue so that the tissue absorbs the compound; and measuring an effect of the compound on the tissue.

In some implementations, the compound is a drug including a muscarinic agonist. In some implementations, the compound is a drug including a stimulant. In some implementations, the process includes measuring the effect comprises measuring one or more of an organization of cell cytoskeletal components of the tissue, an epigenetic change in the tissue, and a gene or protein expression of the tissue.

In some implementations, the one or more parameters comprise a length of the strip, a width of the strip, a thickness of the strip, a shape of the strip, and an elastic modulus of the strip. In some implementations, the tissue is one of a plurality of tissues, and where one or more the plurality of tissues each experience a different loading value. In some implementations, one or more of the plurality of tissues are combined with different compounds The details of one or more embodiments of the microtissues are set forth in the accompanying drawings and the description below. Other features, objects, and advantages of the microtissues and methods for generating them will be apparent from the description and drawings, and from the claims.

DESCRIPTION OF DRAWINGS

FIG. 1A shows a top view of a well and a top view of a strip of bendable material.

FIG. 1B shows a system for generating tissue.

FIGS. 2A-2B show examples of tissue generation.

FIG. 9 shows finite element modeling of a strip.

FIGS. 15-16 shows twitch forces and beat frequencies of a tissue with various chemical stimuli introduced.

Like reference symbols in the various drawings indicate like elements.

DETAILED DESCRIPTION

Figures 3A, 3B, 3C:
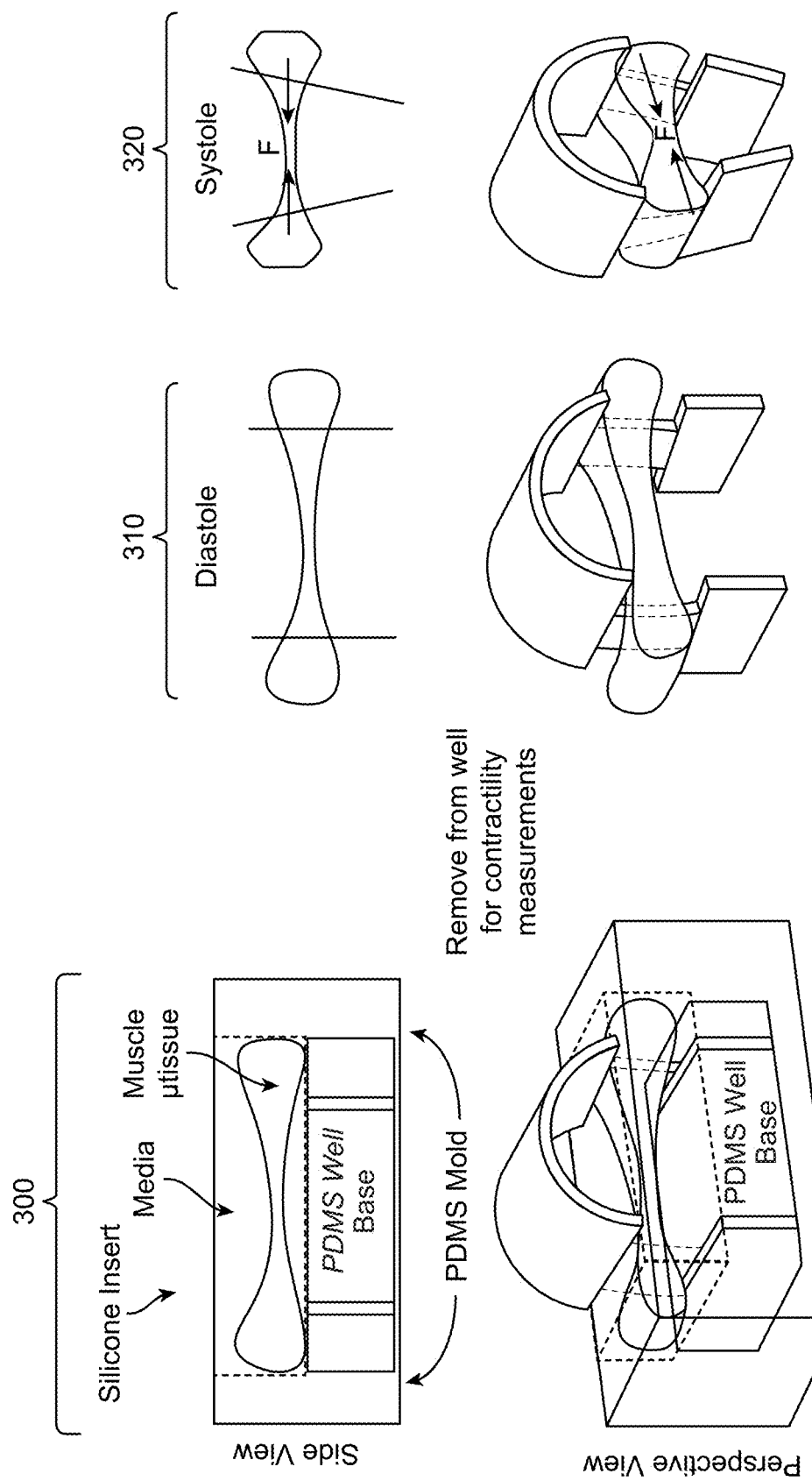
FIG. 3 shows a perspective view of the tissue generation of FIGS. 2A-2B.

Systems and methods for generating 3D microtissues with integrated mechanical loading are described in reference to FIGS. 1A-2B, below.

FIG. 1A shows a top view of a well 100 for generating 3D tissues with integrated loading. FIG. 1A also shows a top view of a strip 112 of bendable material. The well 100 includes a well wall 102, a tissue generation region 104 for generating the tissue from a cell culture. The well 100 includes a first slit 106a that receives a strip 122 at a first end 120a of the strip. The well includes a second slit 106b that receives a second end 120b of the strip 112. The first slit 106a and the second slit 106b are approximately aligned in the well 100. The first and second slits 106a-b are spaced in the well at a length 108. The length 108 is based on a size of the well 100. The length 108 determines what an initial tissue length will be of tissue generated in the well 100. The tissue being generated includes an initial length (e.g., before contraction of the tissue) approximately equal to length 108. Length 108 is typically less than 60 mm (e.g., 10 mm, 20 mm, or and such length required for generating tissue of a desired length), but can be expanded beyond this size for large wells.

A strip 112 of bendable material is configured to be inserted into slits 106a, 106b of the well. The strip is typically formed of PDMS material, but other materials can be used. Here, the term "bendable" refers to any material that is capable of bending and exerting a stress force in compression on a tissue attached to either end of the strip 112. For example, the strip 112 can include a medical grade elastomer. For example, the strip 112 can include a thin thermoplastic above the Tg such as Teflon™ film, polycarbonate film, elastomeric film, etc. When bent, the strip 112 is configured to provide a load based on the parameters (e.g., length, width, thickness, shape, elastic modulus, etc.) of the strip. The load (e.g., stress on the tissue) provided by the strip 112 can range from ~1 kPa to ~10,000 kPa. The load can be tuned based on selection of the parameters of the strip 112. In this way a particular load on the tissue can be selected to provide a stress force on the tissue of a particular value.

The strip 112 can include any geometry needed to tune the strip to exert a particular load on the tissue with which it is integrated. The geometry of the strip 112, including the length 114, width 116, and thickness (dimension 122 of FIG. 1B), are each variable parameters that affect the load that the strip 112 exerts on an integrated tissue. A first end 120*a* of the strip 112 is inserted in slit 106*a* of well 100, and a second end 120*b* is inserted in slit 106*b* of well 100. The strip 112 is configured to bend when inserted into well 100. The length 114 is selected for determining how much the strip 112 bends when inserted into the well 100. Each end 120*a*, 120*b* is sized to fit precisely into slits 106*a*, 106*b*, respectively, so that no cell culture mixture enters the slits.

The well 100 includes a tissue generation region 104 where a mixture of cells with a hydrogel for culture is disposed in the well. The strip 112 includes a first region 118*a* proximate the first end 120*a* of the strip for coupling to the tissue of organic material. The strip 112 includes a second region 118*b* proximate the second end 120*b* of the strip for coupling to the tissue. The first and second regions 118*a*, 118*b* are exposed to the cell and hydrogel mixture when the strip 112 is inserted into the well 100. In some implementations, the first and second regions 118*a*,118*b* are narrower, necking regions compared to the width 116 of the strip 112. The narrower width facilitates tissue attachment to the strip once the tissue forms from the cell culture.

FIG. 1B shows a side view of a system 130 for generating tissue including the well 100 of FIG. 1A and the strip 112 of FIG. 1A. The strip 112 is bent and inserted into slits 106*a*, 106*b* of the well 100. The tissue generation region 104 is shown as only partially filling the well 100. However, the well 100 can be fully filled with a cell culture, and a greater portion of the strip 112 can be exposed to the cell culture. The slits have a depth denoted by dimension 126. Typically, the slits are less than 10 mm deep, but can be made larger for longer strips. Strip thickness 122 can vary and determines how much load the strip 112 exerts on the tissue once the strip and tissue are removed from the well 100 (e.g., in addition to strip length, width, elastic modulus, and shape). While inserted into the well 100, the slits 106*a*,106*b* prevent the strip 112 from moving and limits the load of the strip 112 from being exerted on the tissue. The tissue contracts against the strip while the strip is inserted in the well, and the first and second regions 118*a*, 118*b* are approximately fixed in place. When the strip 112 and tissue are removed, the full loading of the strip is exerted on the tissue.

FIGS. 2A-2B show examples of tissue generation. In FIG. 2A, the strip 112 has been removed from the well 100 and the tissue 200 is contracting, pulling the ends of the strip 112 together to a length 204 that is shorter than length 108 of FIGS. 1A-1B. In some implementations, the tissue 200 contracts by at least 10% of an initial length 108 (e.g., so that length 204 is less than 90% of length 108, respectively). In some implementations, the tissue 200 contracts even more, shortening at least 40% of an initial length 108 (e.g., so that length 204 is 60% of length 108, respectively). Arrows 206 show a stress load exerted on the tissue 200 by the strip 112. Arrows 208 show a contractile force of the tissue. The contractile force 208 can be measured by determining how much the strip 112 has bent during contraction of the tissue 200. This measurement, in combination with the selected dimensions of the strip 112, form a basis for calculating the contractile force 208 of the tissue in a non-invasive manner. For example, no strain gauges need be inserted into the tissue—the measurement process can be passive. The contraction shown in FIG. 2A can be the result of applying electrical stimulation to the tissue 200, as described in further detail, below.

In some implementations, the tissue 200 contracts to a length 204 that can be approximately 10% shorter than an initial length of the tissue. In some implementations, the tissue 200 contracts even more (up to 40% an initial length of the tissue). The tissue is affixed to the strip 112 at regions 202*a* and 202*b* of the tissue. As stated above, the ends of the strip 120*a*, 120*b* can be wider than the regions of the strip 112 to which the tissue is affixed to ensure that the tissue does not slip off the strip once the strip is removed from the well.

FIG. 2B shows a strip 112 integrated with tissue 210. Arrows 206 show a stress load of the strip 112 on the tissue 210. Arrows 212 show a contractile force of the tissue 210. Length 210 can be approximately the same as length 108, or between lengths 108 and 204. Regions 202*a-b* of the tissue are affixed to the strip 112. The tissue 210 may contract less than tissue 200 of FIG. 2A for several reasons. For example, tissue 210 may contract less over time, or a lesser contractile force of tissue 210 may be indicative of disease, etc. The longer length 210 between the attachment regions 202*a*, 202*b* cause the strip 112 to curve less than in FIG. 2A. The reduction in the curvature can be imaged and the contractile force 212 can be compared to a nominal contractile force (e.g., force 208).

A particular embodiment of the tissue generation of FIGS. 1A-2B is now described. A contractile 3D CM tissue is generated as shown in FIG. 3. The potential of the generated tissue as a cardiac model tissue is shown below. The tissue functions as a template to engineer 3D skeletal muscle models. The tissue generation system is configured to enable measurement of twitch forces of the contractile tissues (e.g., also described as µtissues or microtissues), without invasive probes or force transducers. Specifically, a thin, U-shaped, PDMS strip is integrated with 3D tissues and used the change in bending or tissue length as a means to measure twitch force. Images 300 include views of the PDMS strip (e.g., strip 112), PDMS well base (e.g., well 100 of FIG. 1A), and muscle µtissue (e.g., tissue 200 of FIGS. 2A-2B) as they appear during culture. The thin, PDMS strip had a narrow necking region (e.g., attachment regions 118*a-b* of FIG. 1B) tissue attachment. A wide base at each end of the strip (e.g., ends 120*a-b* of FIG. 1B) is hidden in slits in the PDMS well base to constrain the tissue to attach to the necking region of the strip.

Tissue contraction induces bending of the PDMS U-shaped strip, and the force required to induce changes in bending is measured by a simple beam or cantilever bending model, or optionally a more complicated mechanical model of finite element model, of the PDMS strip. Images 310, 320 show the tissue as removed from the well. The wide base of the strip allowed the tissue to be removed from the well with the strip intact to perform a contractility assay. Upon contraction of the tissue, a force (marked F in FIG. 3) induces bending of the PDMS strip.

In some implementations, human ESC-derived CMs are used to engineer initial tissues termed muscle with integrated force indicators (MIFIs). During experimentation, the cardiac MIFIs responded as expected to excitatory pharmacological stimuli and have the potential to serve as in vitro models of human CM function upon further characterization.

The MIFI model serves as a template that can be applied to iPSC-derived CMs for patient specific disease modeling or skeletal muscle myoblasts since the well and strip design readily translate to other contractile cell types. This system has an advantage over traditional PDMS post-bending based tissues because the strip design enables easy removal of the MIFIs from culture wells without damaging or altering tissue architecture, and also enables the tissue to contract in a non-constrained manner. This allows investigation (e.g., high-throughput assay investigation) of the effect of increased mechanical load on these cardiac or skeletal muscle model tissues. The strips generate a stress field that influences cells of the tissue to align along the long axis of the well. Initially, full force of the strip is partially hidden because the PDMS well base does holds the ends of the strip in place during culture. When the MIFI tissues are removed from the PDMS wells, the applied load to the MIFI increases, forcing the cells to work against the strip to maintain tissue architecture. Thus, this system serves not only as a tool to better understand cardiac and skeletal muscle tissue in normal and disease states but to also allow investigation of combinatorial effects of various small molecule or drug therapies with muscle exercise. Alternatively, this system serves for testing the effects of one or more drug compounds alone, independent of muscle exercise.

To generate the tissue, well molds are designed (e.g., well 100 of FIG. 1A) for casting PDMS for tissue culture. Initial prototypes can be printed with acrylonitrile butadiene styrene (ABS) plastic. Final molds can be printed with a 3D printer.

In some implementations, to create wells from plastic molds, Sylgard™ 184 PDMS (Dow Corning) is mixed at a 10:1 weight ratio of base to curing agent at a 2 minute 2000 RPM mixing cycle and a 2 minute 2000 RPM defoaming cycle. Universal mold release spray is sprayed onto plastic molds to facilitate tissue removal. PDMS is poured until the molds are filled. In some implementations, PDMS wells are degassed for 30 minutes and cured in a 65° C. oven for 2 hours before being removed from the plastic molds.

Well strip (e.g., strip 112) geometries are selected based on the target stress to induce on the tissue. The strip is cut from a sheet of pliable material (e.g., PDMS or other similar material). In some implementations, dogbone-like strips are formed from non-reinforced, 0.005" thick medical PDMS sheeting, though the parameters of the strip (e.g., length, width, elastic modulus of the material etc.) can be adjusted based on a target stress (in other words, the load that the tissue contracts against). In some implementations, the strips are mounted onto glass microscopy slides and imaged with a VHX-5000 digital microscope to measure thickness. Typically, the average of three measurements for each strip is used for later analysis in the contractility assay.

For verifying elastic modulus of the strips, the strip samples are mounted on a uniaxial tensile testing machine (e.g., using an Instron®) and strained at a rate of 1 mm/minute until >10% strain was reached. Sample cross-sections are calculated from average optical measurements of the individual strips prior to testing. Typically, strip thicknesses are obtained by averaging three random thickness measurements per strip (e.g., using a VHX-5000 digital microscope). Stress is calculated by dividing measured force by measured cross-sectional area. Stress is plotted against strain, and the linear curve fit is obtained for the first 10% of strain. For example, slopes of the curves of sample strips were averaged to obtain a final measurement of 3.10 MPa for the elastic modulus of PDMS strips. The elastic modulus was used for modeling the force required to bend strips to specific conformations for the contractility assay.

A particular implementation for culturing cells for tissue generation is described below, but other similar implementations are possible. Cells for cell cultures are typically kept in continuous culture in 6-well tissue culture treated plates pre-coated with 12 µg/cm2 of Geltrex™ and kept at 37° C. and 5% $CO_2$. In some implementations, all media are supplemented with 1:1000 Mycozap-CL (Lonza). In some implementations, to pre-coat well plates, Geltrex™ is diluted in 4° C. DMEM/F12 to a final concentration of 11411 g/mL before pipetting 1 mL/well. Plates are then incubated with Geltrex™ at room temperature for at least 1 hour prior cell seeding or are stored at 4° C. for up to 1 week. In some implementations, cells are rinsed with 1×PBS (GE Healthcare) and incubated with TrypLE™ Express for 5 minutes. The cells are then detached by pipetting, transferred to DMEM/F 12 stopping media and centrifuged at 200 G for 5 minutes. In some implementations, media are aspirated from the cell pellet, and cells were re-suspended and seeded at $13.1 \times 10^3$ cells/cm² in Essential 8™ media (E8) supplemented with 5 µM Y27632 (System Bioscience). After 24 hours Y27632 supplemented E8 was exchanged for E8 media daily until cells reached 80% confluence, at which point cells were passaged or differentiated.

For preparing the cell cultures, the following process is typical, but similar processes are possible. To induce differentiation, on day 0, cells are rinsed with 10×PBS and 3 mL/well of RPMI 1640 basal media supplemented with 1:50 B27 without insulin (RPMI/B27) and 6 µMCHIR99021 (LC Laboratories). On day 2, cells are washed with 1×PBS before adding 3 mL/well of RPMI/B27 with 2 µM Wnt-059 (Selleck Chemicals). On days 4 and 6, the media are exchanged for 3 mL/well of RPMI/B27. On days 8 and 10, the media are exchanged for 3 mL/well of CDM3: RPMI 1640 basal media supplemented with 500 µg/mL of O. saliva derived recombinant human albumin (RHA) (Sigma-Aldrich) and 213 µg/mL of L-ascorbic acid 2-phosphate (AAP) (Sigma-Aldritch). At day 12, if CMs are visibly beating, cells were passaged for purification.

For purification, differentiated cells are passaged by washing with 1×PBS and incubated in TrypLE™ Express for 15 minutes at 37° C. Cells are released from plates by pipetting into DMEM/F 12 stopping media (2 mL/well) and are then centrifuged at 200 G for 7 minutes. Cells are seeded on Matrigel™ (Corning) coated 6 well plates. The plates were coated with Matrigel™ following the same protocol used to coat plates with Geltrex™. The cells are re-suspended in CDM3L (RPMI 1640 without D-glucose supplemented with 500 µg/mL RHA, 213 µg/mL AAP, 7.1 mM sodium DL-lactate (Sigma-Aldrich) and 5 µM Y27632) media. Three mL/well of CDM3L (without Y27632) was then exchanged 24 hours after seeding and at day 4. At day 7, cells were passaged by rinsing with 1×PBS, incubating for 15 minutes in TrypLE™ Express at 37° C., centrifuged at 200 G for 7 minutes, and were then used for experiments.

Human Cardiac Ventricular fibroblasts are used at <15 doublings, and are cultured at 37° C. and 5% $CO^2$. Cells are cultured in FB Growth Medium-3 (FGM3) made from the FGM-3 BulletKit™ (Lonza) consisting of FBM supplemented with 0.1% rhFGF-B, 0.1% insulin, 10% fetal bovine serum, and 0.1% 1000× gentamicin/amphotericin-B. Upon thawing, cells are resuspended in FGM3 and seeded at ~3.5×10$^3$ cells/cm$^2$. After reaching 80% confluence, cells are rinsed with 1×PBS and incubated with 0.25% Trypsin-EDTA (Thermofisher) for 3-5 minutes at 37° C. After cells began to detach, 2 mL Trypsin Neutralizing Solution (Lonza) are added per mL of TrypsinEDTA, and the cell suspension is centrifuged at 220 G for 5 minutes. The media supernatant is aspirated, and cells are either re-suspended in FGM3 and passaged at a density of 3.5×10$^3$ cells/cm$^2$ or used for casting MIFIs.

C2Cl2s are cultured according to manufacturer specifications. Typically, cells used in experiments are kept below passage 12 and below 80% confluence while in continuous culture. C2Cl2 cells are kept in growth media (GM) consisting of high glucose DMEM (Corning) supplemented with 1% 100× Penicillin-streptomycin (Thermofisher), 1% 100×L-glutamine (Thermofisher), and 10% fetal bovine serum (JR Scientific). Generally, when cells reach 80% confluence, the cells are passaged by washing with 1×PBS and incubated with 0.05% Trypsin>EDTA for 3-5 minutes. Cells are then resuspended in GM at a 2:1 ratio of GM to Trypsin-EDTA and centrifuged at 2000 RPM for 5 minutes. The supernatant is aspirated from the cell pellet, and cells are reseeded at ~6.5×10$^3$ cells/cm$^2$ in a new flask or cast in MIFI construct.

Prior to tissue culture, PDMS wells are cleaned by sonicating in 50% ethanol for 30 minutes. The PDMS strips and vacuum grease can be UV-treated for 15 minutes prior to use. PDMS wells can be dried using a nitrogen air gun and then incubated with 1% w/v Pluronic™ F-127 (Sigma) for 3-5 minutes to prevent cell attachment to PDMS. Typically, Pluronic™ F-127 is aspirated and wells are rinsed 3 times with 1×PBS. The strips (e.g., strips 112) are then placed in the wells by securing both ends in slits (e.g., slits 106a-b of FIG. 1A) in the base of the PDMS wells. Before strip placement, the bottom of the PDMS well can be coated with vacuum grease, and wells are then firmly placed in the well of a culture plate. The culture plate used in experimentation was a 6-well plate. However, well plate size include other sizes, such as a 48 well plate or a 96 well plate. Wells with strips are then used immediately or sterilely stored for later use.

For experimentation purposes, rat tail Col I (Corning) was gelled following the neutralization reaction using 1N NaOH (Sigma) as recommended by the manufacturer. MIFIs may be generated using multiple collagen concentrations. In one example they are cast with final concentrations of 2 mg/mL (e.g., 2, 5, 10, etc. mg/mL) Collagen I, 20% v/v Matrigel™, 10% 1×PBS (Hyclone), 2.3% 1 NNaOH, and 18.75×10$^6$ cells/mL for CMs and 15×10$^6$ cells/mL (or other similar concentrations) for C2Cl2s. Other materials (e.g., fibrin) can be substituted for the cell culture. Additionally, the concentrations of cells can be increased or decreased from these values, which can be is done to tune tissue density. When NIICV-Fs were included with HUES9-CMs, they were mixed at ratios of 10 or 20% of total cell concentration. After manual mixing, the cell/gel mixture was pipetted gently into wells (80 μL/well) to avoid creation of bubbles. To prevent MIFIs from coming out of the wells due to vigorous beating at later dates in culture, No. 2 55×45 mm cover glasses can be cut into rectangles <3 mm in width and at least 10 mm in length using a diamond tip pen, inserted on top of PDMS wells but under strips and secured with vacuum grease. The MIFIs were placed in a 37° C. incubator for 45 minutes to allow gelation of the Col I prior to addition of culture media. CMs were cultured in RPMI 1640 with 1% knock-out serum replacement (Thermofisher) and 1:000 Mycozap. In some implementations, C2Cl2s are cultured in GM for 1 week before switching to DM. CM and C2Cl2 media can be exchanged every 48 hours. This particular process can vary depending on the cell culture being developed. MIFIs were kept in culture up to 14 days before removal from wells for the contractility assay.

MIFIs can be imaged on a stereo microscope with oblique illumination during culture for top down images of tissue area. Images are converted to grey-scale, thresholded, and then converted to an 8-bit binary in order to distinguish the tissue area from the rest of the well. The percent area of the tissues was tracked in this way for the duration of culture.

MIFIs were removed from wells using forceps and were transferred to a 35 mm petri dish filled with 37° C. Tyrode's solution (1.192 g HEPES, 0.203 g MgCl$_2$, 0.403 g KCl, 7.889 g NaCl, 0.04 g NaH$_2$PO$_4$, 0.901 g C$_6$H$_{12}$O$_6$, and 0.265 g CaCl$_2$) per liter of distilled water, pH 7.4). MIFIs were anchored by placing the wide base of the strip into a slit in a PDMS block glued to the bottom of the stimulation dish. The Tyrode's bath was maintained between 30° and 37° C. using a heated stage regulated by an in house Lab VIEW program. Videos of samples were taken using a Nikon™ D5100 DSLR camera mounted on a Nikon™ SMZ1500 stereomicroscope. Samples were paced from 2-10 Hz using parallel platinum electrodes placed 2 cm apart and immersed in Tyrode's solution. Samples were stimulated with 40V using a 10 ms square pulse wave. Shorter pulse durations can also be used (e.g., 2 ms, 4 ms, 6 ms, etc.).

Carbachol and isoprenaline were mixed to stock concentrations of 5 mM in 1× Tyrode's solution. 5 mM epinephrine stock solution was made by dissolving epinephrine at 500 mM in HCl before diluting with Tyrode's to a final concentration of 5 mM. Caffeine was dissolved directly in Tyrode's to make a stock solution of 20 mM. All stock solutions were diluted further with Tyrode's to reach concentrations of 50 nM, 500 nM, 5 μM, and 50 μM for carbachol, isoprenaline, and epinephrine. Caffeine was used at 500 μM or 5 mM concentrations. These concentrations were used because this range had been previously demonstrated to elicit changes in force exertion and beats per minute (BPM) from cardiac tissues in a dose-dependent manner. During the contractility assay, MIFIs were washed 3× with Tyrode's between drugging conditions, and videos of constructs in Tyrode's only were taken between different drug conditions to determine if the MIFI had recovered to its initial, predrugged state.

Samples were fixed in 4% formaldehyde (electron microscopy sciences) in PBS with 1:200 Triton-X 100 (Fisher Scientific) for 1 hour followed by three 30 minute washes in PBS. Samples were blocked in 5% goat serum in PBS overnight at 20° C. followed by three 30 minute washes in PBS. Mouse anti-sarcomeric-α-actinin (Sigma-Aldrich) was diluted to 1:100 in PBS, and samples were incubated overnight at 20° C. in 500 μL of antibody solution in 24 well culture plates to ensure coverage of the 30 tissues. Samples were then washed 3 times for 30 minutes each in PBS before incubating with 1:200 DAPI, 3:200 phalloidin tagged with Alexa-Fluor® 488, and 1:1000 goat anti-mouse antibody tagged with Alexa-Fluor® 555 in PBS at 20° C. overnight. After the final incubation step, samples were rinsed 3 times for 30 minutes each in PBS before imaging or storing in PBS.

Finite element modeling of bending PDMS strips was used to create lookup tables for strips ranging in thickness from 125 to 154 μm. FIG. 9 shows modeling data 930 for strips 900, 910, and 920. The elastic strip (e.g., strip 112) was modeled as 3D deformable extruded solid, with extruded thickness varying between 125 and 154 μm. The elastic strip was considered as linearly elastic, isotropic and incompressible material, with Young's modulus equal to 3.09 MPa according to elastic modulus measurements. The section of the elastic strip was considered as solid homogeneous. The force-driven bending simulation was designed to mimic the experimental procedure. One static general analysis step was used where the elastic strip was deformed by application of equal contractile force in three parallel axial connectors placed in the regions where the tissue was attached during the experiment, so that the total force would equal the sum of the contractile force of the three connectors. The total force ranged between 60 and 155 μN for the experimentally measured tissue length that corresponded to the deformed length of the connectors. Additional boundary conditions were imposed based on geometrical symmetry. The general analysis step did not have automatic stabilization applied, and the step increments were assigned automatically. Finally, the finite element mesh was composed of 20-node quadratic, hybrid, reduced integration brick elements. From this model, the change in tissue length could then be used to calculate the force necessary to bend the strips to these conformations. Length changes of contracting MIFIs were tracked, and resulting length data was used to calculate the corresponding force based on tissue length and strip parameters (e.g., thickness, width, length, elastic modulus, and shape).

To approximate tissue cross-sectional area to normalize measured twitch forces, microtissue width and thickness were measured using image-processing techniques. Specifically, width and thickness measurements were taken per construct, one within 1 mm of either strip attachment site and 1 mm from the middle of the tissue. Tissues were assumed to have an ellipsoid cross-section, and these width and thickness measurements were used as the long and short diameters of the calculated ellipsoid cross-section. Additionally, muscle cross-sectional area was approximated to normalize force per muscle area by assuming full cell coverage within the outer 100 μm diameter of constructs. Muscle area was then calculated as 90% or 80% of full area for 10% and 20% FB tissues, respectively. In this way, muscle cross-section was likely over estimated, but this allowed for the normalized force to be an underestimation for a worst case scenario. Specific force was calculated by dividing twitch force by the approximate cross-sectional area and for approximate muscle cross-sectional area for each individual tissue.

Figure 6J:
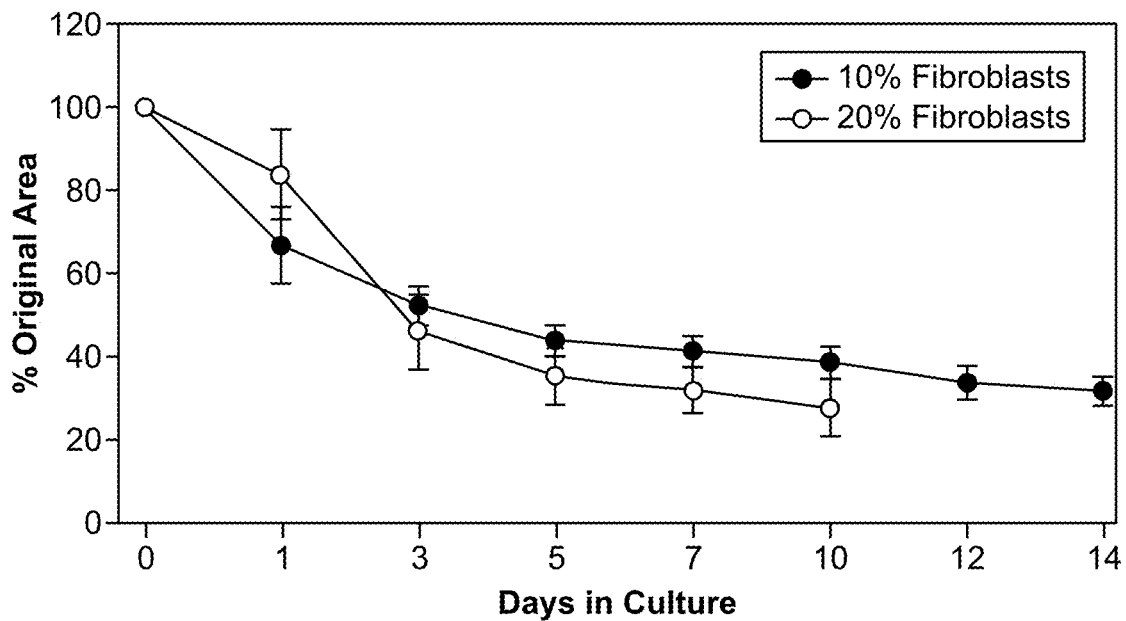
FIG. 6 shows images of cardiac muscle tissues with cardiomyocytes and with 0%, 10% and 20% cardiac fibroblast cocultures.
Figure 6K:
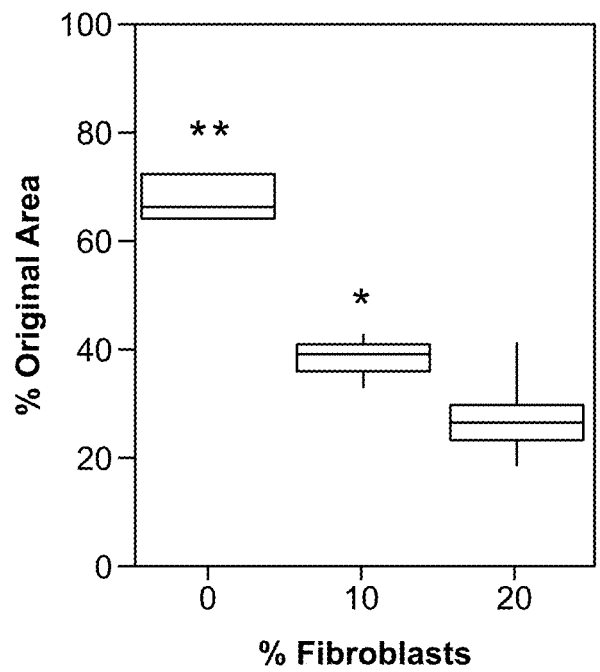
Figure 14A:
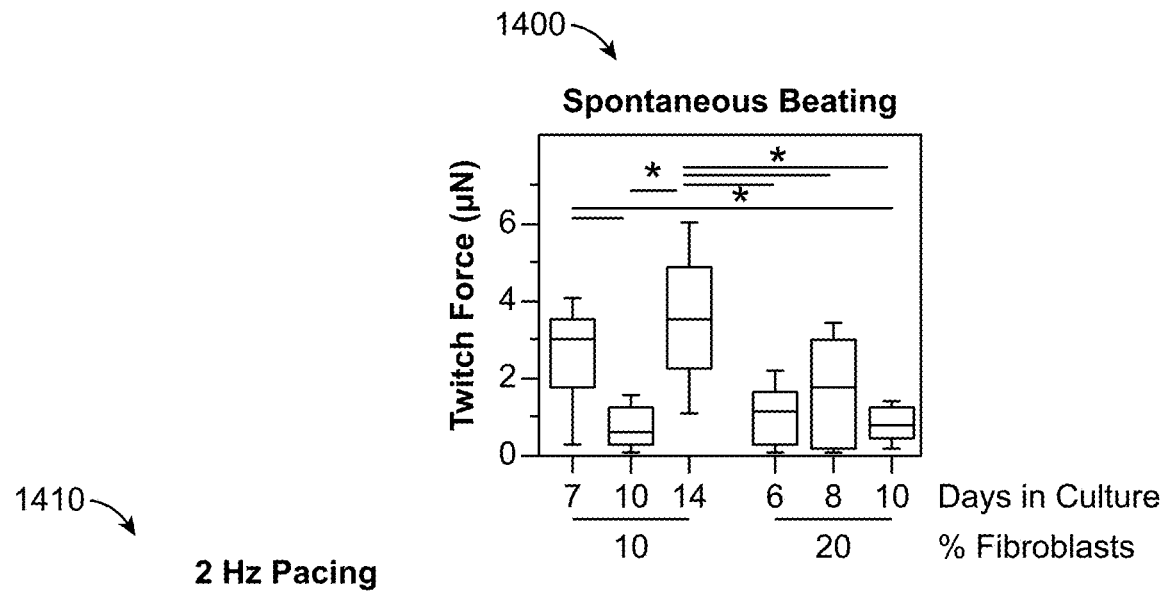
FIG. 14 shows twitch forces and beat frequencies of a generated tissue.
Figure 14B:
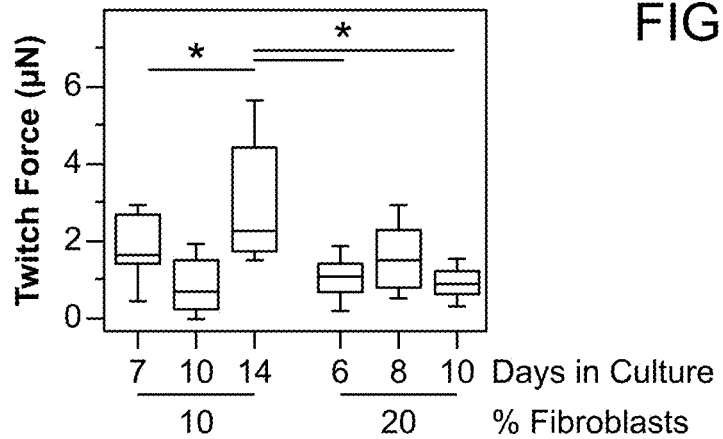
Figure 14C:
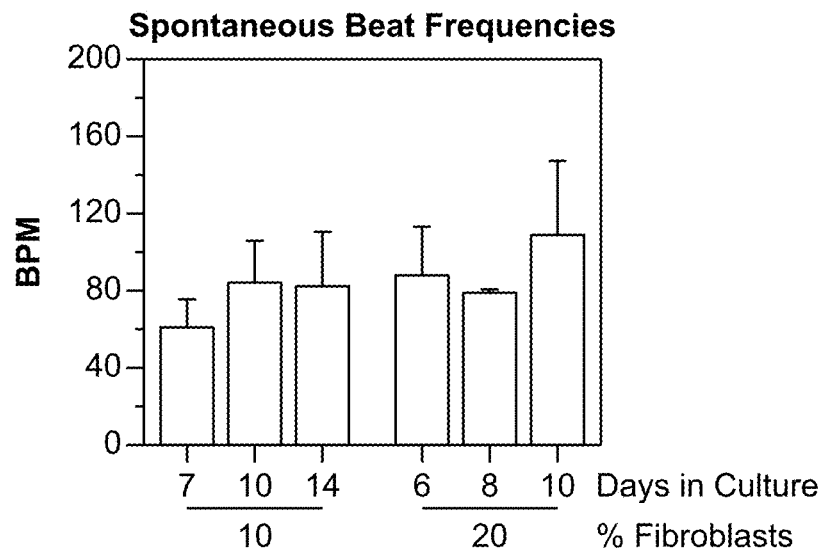
Figure 15A:
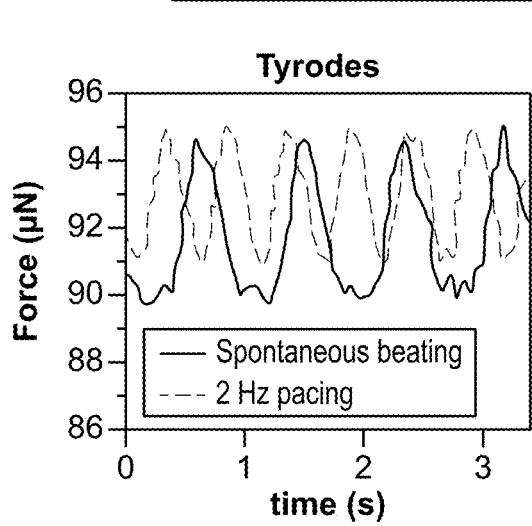
Figure 15B:
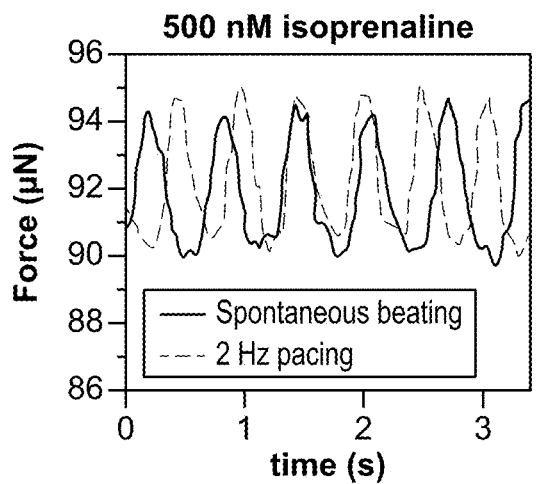
Figure 15C:
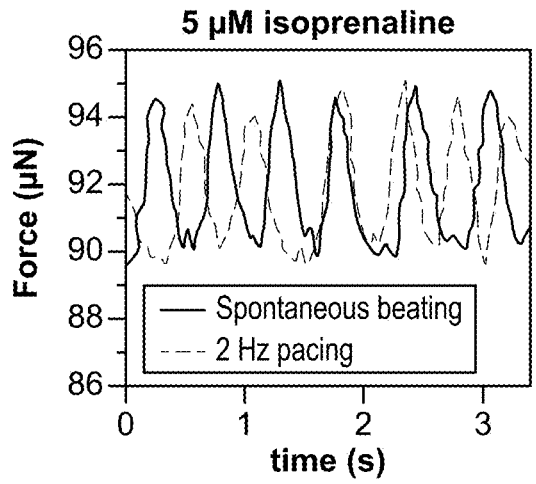
Figure 15D:
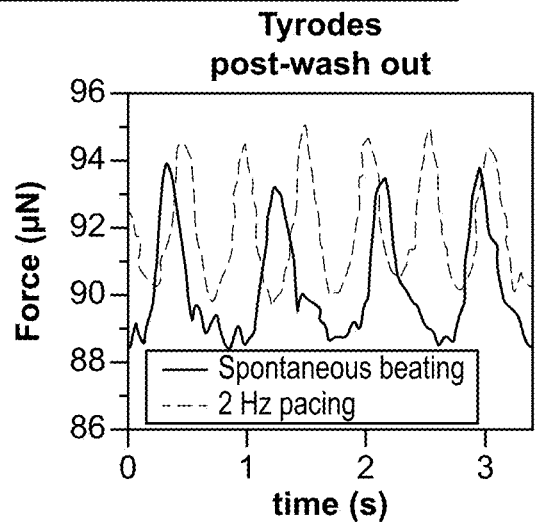
Figure 15E:
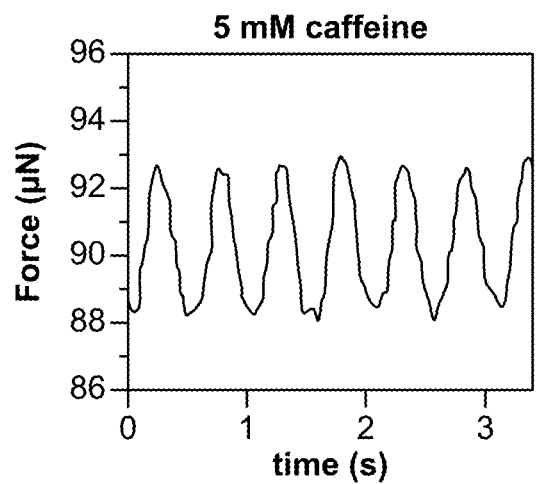
Figure 15F:
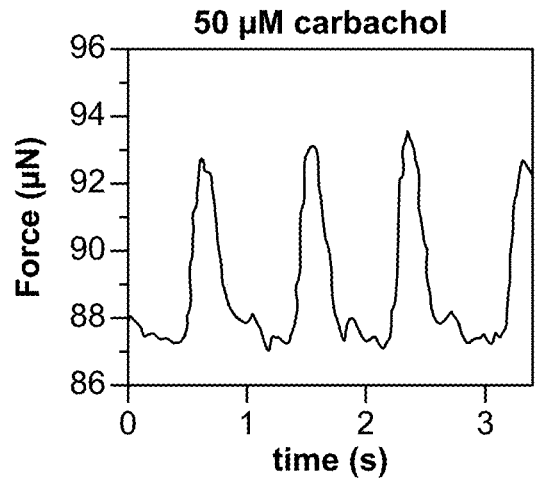
Figure 15G:
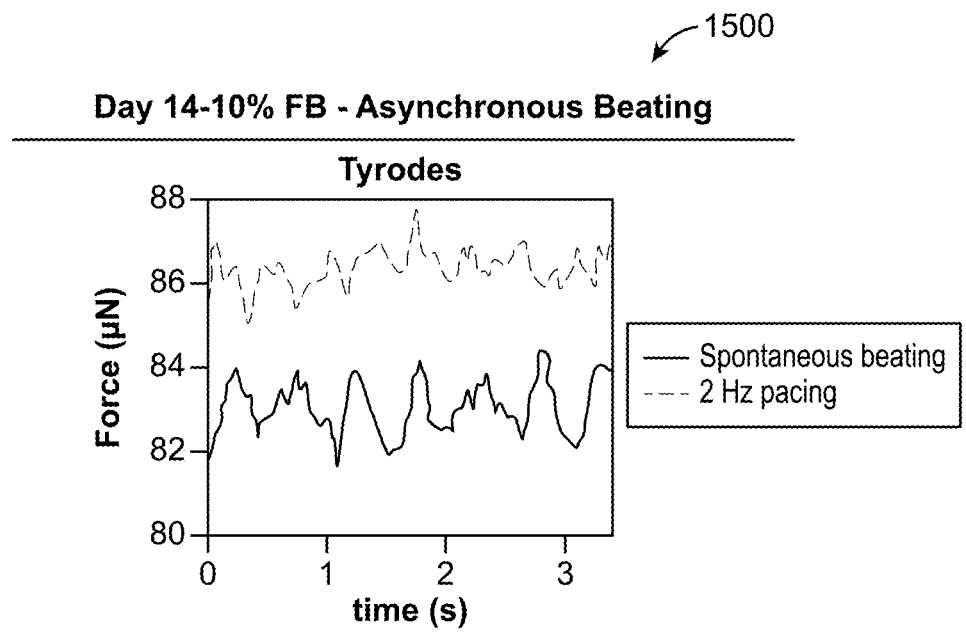
Figure 15H:
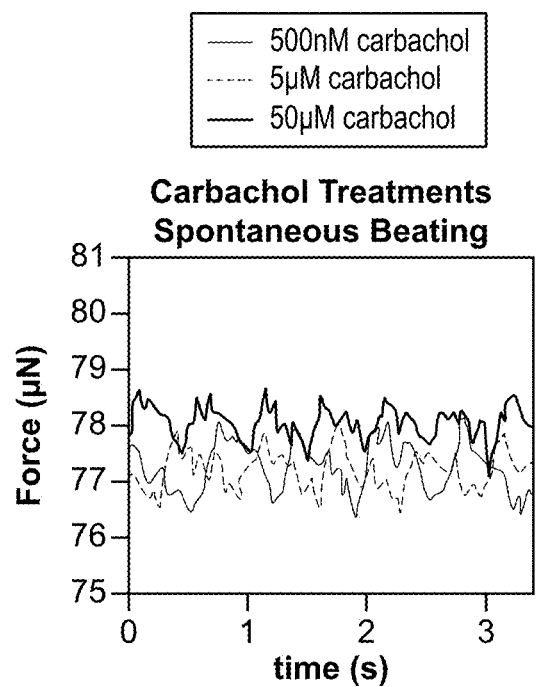
Figure 15I:
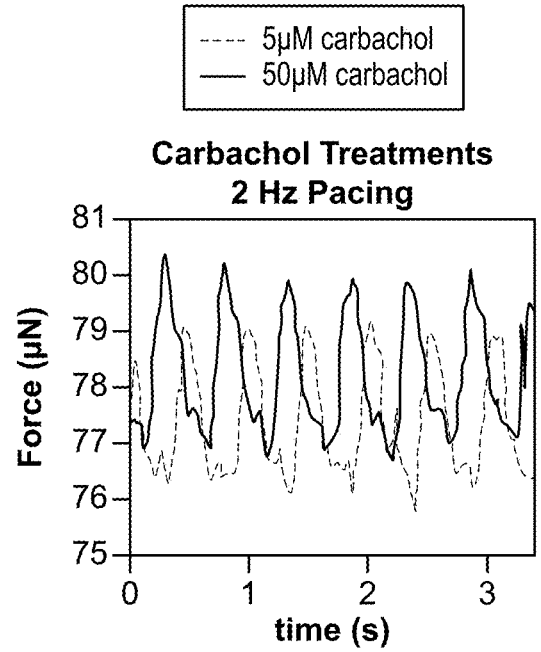

ANOVA on ranks was performed on data presented in FIG. 6, FIG. 14, and FIG. 16 graph 1640 using the Dunn's method posthoc test, and ANOVA on ranks with post-hoc Tukey test was performed as shown in FIG. 16 graph 1650. Two-way ANOVAs with Holm-Sidak post-hoc comparisons were performed for FIG. 16 graphs 1600, 1610, and 1620. A Mann-Whitney Rank Sum test was performed on FIG. 16 graph 1630. A One-Way ANOVA was performed on data in FIG. 14 graph 1410 with no post-hoc test as no significant differences were found. Differences were considered significant at p≤0.05. Sample sizes for twitch force graphs in FIG. 14 graphs 1100, 1110 represent five technical replicates/sample, i.e. if n=30, then five beats/sample for six separate samples are represented.

Returning to FIG. 3, a system for forming contractile, 3D muscle tissues that could be easily removed from culture wells and analyzed in a side on contractility assay is shown.

A U-shaped, thin PDMS strip (e.g., strip 112) is an indicator to track force exerted by beating tissues. The strip is designed to have bases hidden in slits in the PDMS culture well and a narrower attachment around which the tissue can polymerize, compact, and mature. As discussed in reference to FIG. 1A-2B. This relatively wide strip base enables eventual removal of the tissue from the well, at which point, contraction of the beating cells induced a change in tissue length and bends the strip, shown at 310, 320 of FIG. 3. In this way, MTFIs were easily assessed for overall tissue beat frequency and muscle force generation. Typical 3D construct designs in the past had PDMS posts that dictated tissue geometry designed as a part of the well itself, and removal of the tissue from the well would result in a contractile tissue with no load to work against relative to itself.

Figure 4:
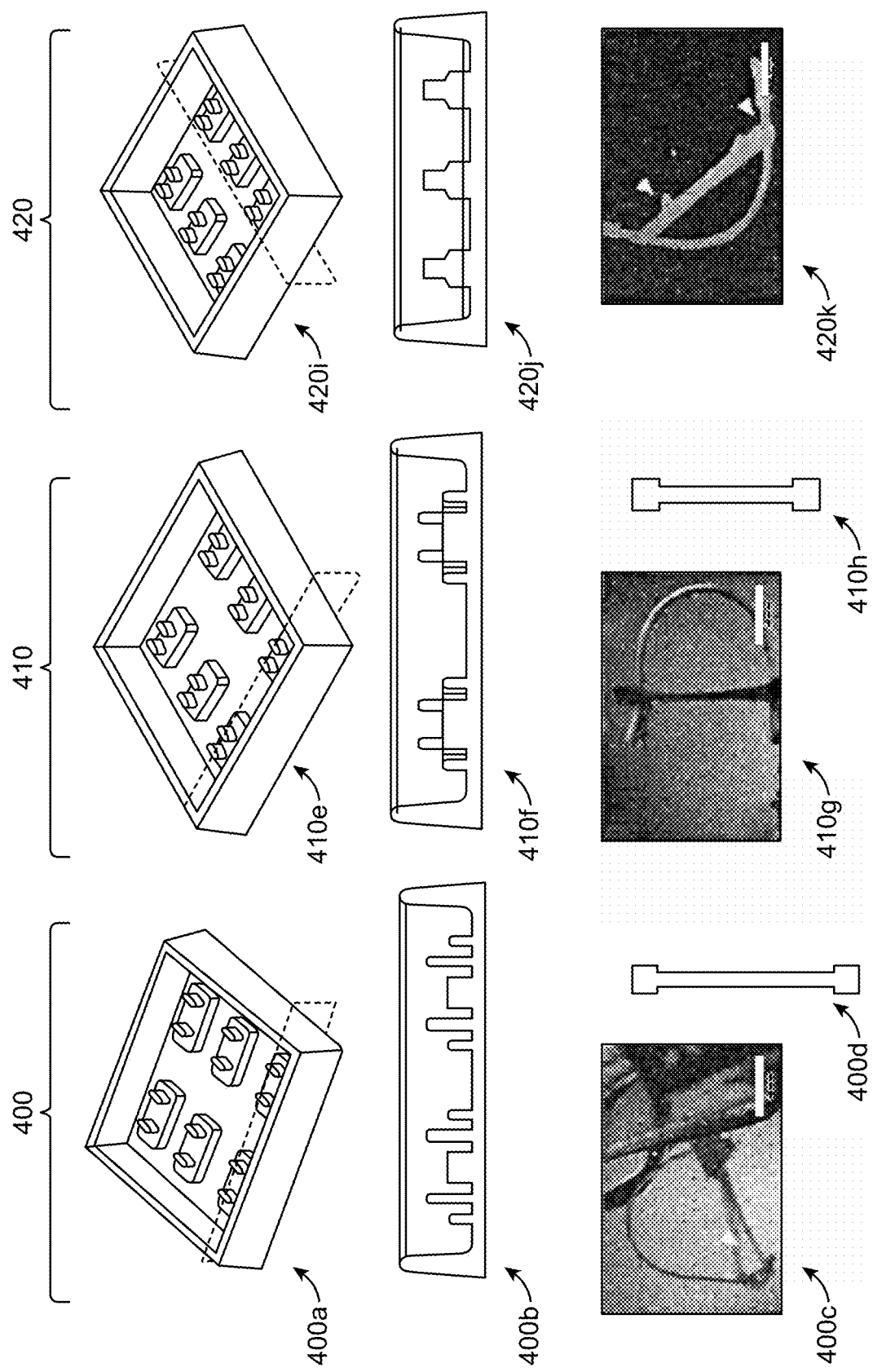
FIGS. 4-5 show examples of wells, well plates, and strips.

Turning to FIG. 4, in order to allow removal of the tissue while still maintaining adherence to post-like structures, PDMS molds were designed to have a in the base of the well between 2 small posts. U-shaped, thin, PDMS dog bone-like strip configured for being inserted orthogonally to either end of the tissue during the Collagen I polymerization process, but hidden between the PDMS posts. Initial designs were tested using C2Cl2 tissues, tissue attachment, but large holes resulted from the double post design. To reduce resulting holes in the tissues but maintain the classical post design, the inner posts are removed and made the wells made smaller. The resulting MIFIs appeared to have improved tissue integrity at the attachment sites, shown by 410g. After successfully removing the inner posts for Design 2, we wanted to determine if posts were necessary or if the PDMS strip alone was enough of an anchor point on either side of the well for tissues to attach and compact without any posts. Well 420 was developed to determine tissues could be cast around the strip. C2Cl2 MIFIs attached and compacted with no apparent issues in well 420; however, the well slits for strip placement were wide enough to allow the cell+gel mixture to seep into the slits, which were ~1 mm wide, before polymerization had occurred. This resulted in small tissue overhangs shown in 420k. Tissues were able to move up the strips since there was nothing restricting them to the initial attachment sites after removal from wells 420.

FIG. 4 shows an iterative plastic mold and PDMS strip design process. At 400a, a perspective view of CAD model of a plastic mold design is shown, intended to hide the strip between 2 PDMS posts on either side. The mold is the negative of what PDMS wells look like. A cutaway view of the dotted black rectangle shows side view 400b of Design 1 where arrows point out what will become PDMS base slits and additional arrows point out what will become PDMS posts. Image 400c shows that C2Cl2 MIFI created using Design 1 resulted in the possibility of large holes in the tissue around the strip because it was 'hidden' between 2 PDMS posts (see arrows). Strip 400d is a PDMS strip with dimensions for mold Design I. Image 410e shows a perspective view of CAD model of plastic mold Design 2, intended to hide the strip against 1 PDMS post on either side to decrease hole size in tissues. This is the negative of what PDMS wells would look like. A cutaway view 410f of the dotted black rectangle shows a side view of Design 2 where arrows point out what will become PDMS base slits and additional arrows point out what will become PDMS posts. Image 410g shows a C2Cl2 MIFI created using Design 2 that has better tissue integrity around the attachment sites. Strip 410h is a PDMS strip with dimensions for mold Design 2. The strip length was shortened to match the shorter well dimensions after removal of inner posts. Image 420i includes a perspective view of CAD model of plastic mold Design 3, intended to completely replace posts with the strip. This is the negative of what PDMS wells would look like. A cutaway view 420j of the dotted black rectangle shows a side view of Design 3 where arrows point out what will become PDMS base slits. Image 420k shows a C2C12 MIFI created using Design 3. We observed small overhangs of tissue formed from seeping into the base slits before the Collagen I had polymerized and the tissue was beginning to slip up the strip (arrows). The scale bars for 400c and 410g are 4 mm. The scale bars for 420k are 3 mm.

Figure 5:
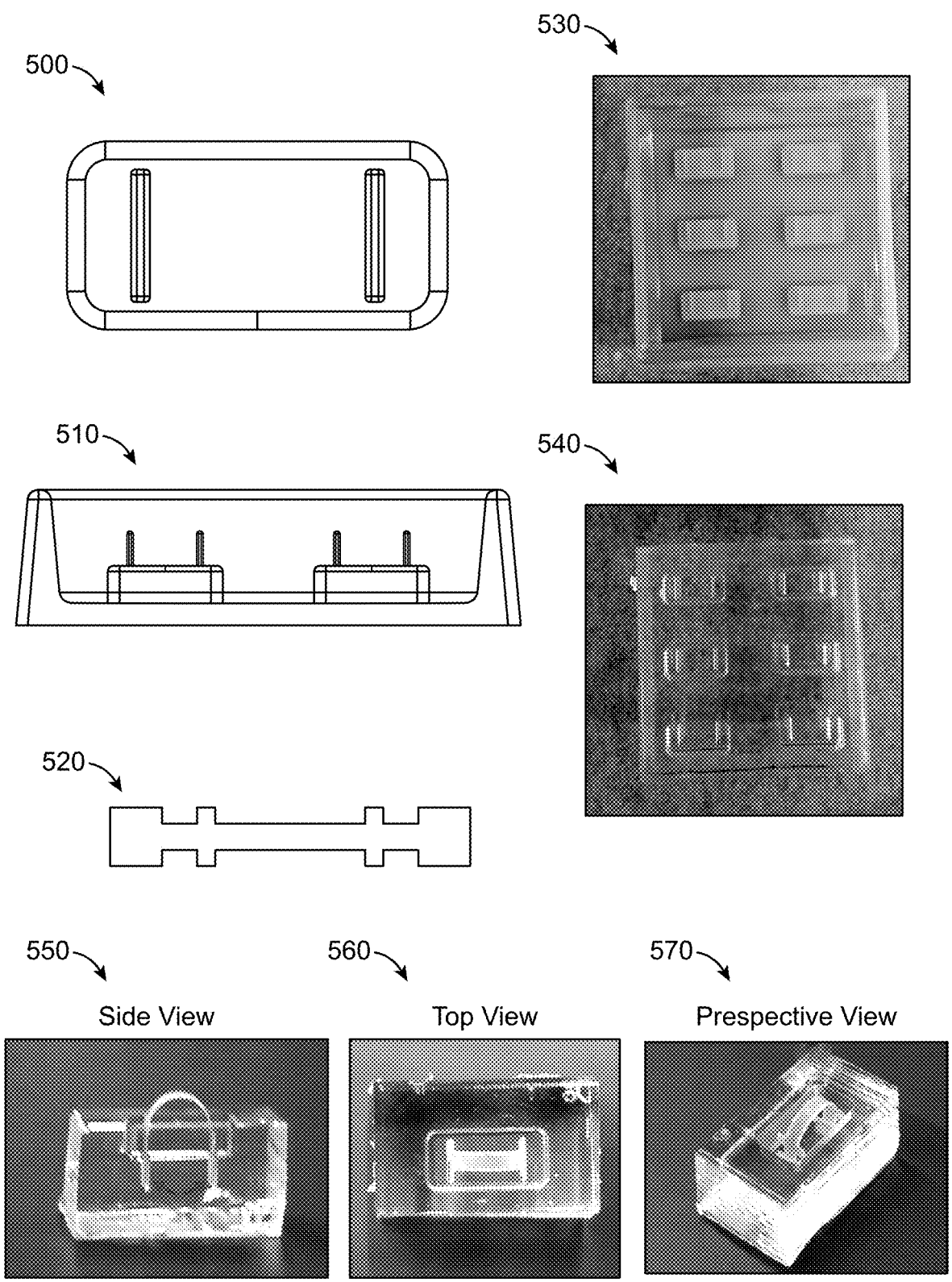

In some embodiments, as shown in FIG. 5, PDMS well 500, 510 includes 5×10 mm wells and strip slots that are 500 µm wide (to prevent tissue overhangs) and 3 mm deep. The thin, PDMS strip 520 (e.g., equivalent to strip 112 of FIGS. 1A-2B) was designed to have a base to sit flush within the well slit, a 1.5 mm necking region for the cast tissue attachment, and a small 3.4×1 mm flap above the attachment region to prevent tissue slippage. These strips were laser-cut from pre-made 127 µm thick PDMS sheeting, and the final PDMS well with strips placed in allowed for the base of the strips to sit flush against the well slit portion, shown in in images 550, 560, and 570.

Image 500 shows a top down view of the dimensions of the raised portion of the plastic mold used for casting wells for MIFIs. Smaller rectangles (arrows) served as the strip slots in the PDMS well. Image 510 shows the final design of the well (e.g., well 100), which had a base with 3 mm deep slots to 'hide' strip base in the PDMS well during culture. Image 520 shows a preferred strip design (e.g., strip 112) included 3 mm×3.4 mm regions to be hidden in the PDMS well base, a 1 mm wide necking region for tissue attachment, and a small 3.4 mm wide overhang to prevent the tissue from sliding up the strip. Image 530 shows a top down image of the plastic master mold and image 540 shows resulting PDMS wells. Images 550, 560, and 570 are side, top, and perspective views, respectively, of the strip placed in the final well design. The strip can be seen resting flush against the in the PDMS base slits (arrows). All dimensions are in mm.

Turning to FIG. 6, day 1 images 600a-I show constructs cast with HUES9-CMs and 10% FBs (600a), 20% FBs (600b-c), 0% FBs (600d). Further shown are day 10 images of 10% FBs (600e), 20% FBs (600f-g), and 0% FBs (600h), which only show visibly more compact tissues in tissues seeded with FBs compared to HUES9-CMs only. ~30% of tissues with 20% FBs exhibit irregular remodeling and break away from the strips as seen in image 600g. 10% FB (image 600i) tissues continue to uniformly compact at day 14 in culture. Graph 600j details this phenomenon and includes plots of tissue compaction over time, as represented by percent of the original area, show that both 10% and 20% PB tissues have slowed compaction rates after the first three days in culture. Tissues with 20% FBs have less uniform compaction compared to 10% FB tissues, as shown by larger standard deviation bars associated with these tissues. Graph 600k shows Day 10 of compaction area, as represented by percent of original area, is significantly affected by the addition of FBs. Dotted black lines outline the tissues and scale bars are 2 mm.

In an initial study to determine if Col I gels with HUES9 derived CMs induced bending of PDMS strips, tissues with CMs only were cast in the prototyped well design and allowed to culture for 10 days after casting, shown in images 600a,d,c,d. While contraction of MIFIs induced bending of strips, the CM-only tissues did not significantly remodel the surrounding Col I gel. This was problematic as these tissues are diffusion limited to having viable cells within the outer 100 µm of gel, and the initial tissue dimensions (~1×10×5 mm) were an order of magnitude outside of the diffusion limits of non-vascularized tissues.

In order to engineer more cell-dense MIFIs that compacted over time, we added cardiac ventricular FBs to assist the CMs in remodeling the surrounding Col I+Matrigel™ mixture, a method that had been previously shown to work in 30 engineered cardiac muscle. FB populations used in the literature were derived from varying sources and may behave differently than the commercially available FBs we used, so we added 10% or 20% FBs to MIFIs as ranges of 3%-30% FBs had been reported as effective. We found that the addition of FBs resulted in visual compaction of the MIFIs, and representative images of those with 10% FBs at Days 1, 10, and 14 showed relatively uniform compaction as far as 2 weeks in images 600a, 600e, and 600i. For 20% FB MIFIs some tissues displayed uniform compaction by Day 10 in culture shown in images 600b,f, but as many as 50% of constructs tore due to less uniform compaction by the higher FB population shown in images 600c,g. Compaction area of these tissues were tracked from Day 0, when all wells were 100% filled (by area), to Day 10 or 14, depending on FB composition. Both FB concentrations resulted in compaction to ~50% of initial area by Day 3 after casting (10% FB—52.2%, 20% FB—46.0%) shown in graph 600j. By Day 10, 20% FB MIFIs had compacted to ~10% less area (27.8%±6.62) than 10% FB MIFIs (38.5%±3.88), but as previously mentioned, these tissues were less uniformly compacted. 10% FB MIFIs were easily maintained in culture for at least 14 days, when they reached 31.7%±3.26% of their original area shown in graph 600j. Thus, while 20% FB MIFIs were significantly more compacted by Day 10 than the 10% and 0% FB MIFIs, the compaction was less predictable and often resulted in up to 50% sample loss due to breakage graph 600k. The 10% FB MIFIs were able to compact significantly more than 0% FB MIFIs 600k and were able to be maintained for longer culture times due to more uniform compaction by the smaller FB population.

Figure 7A:
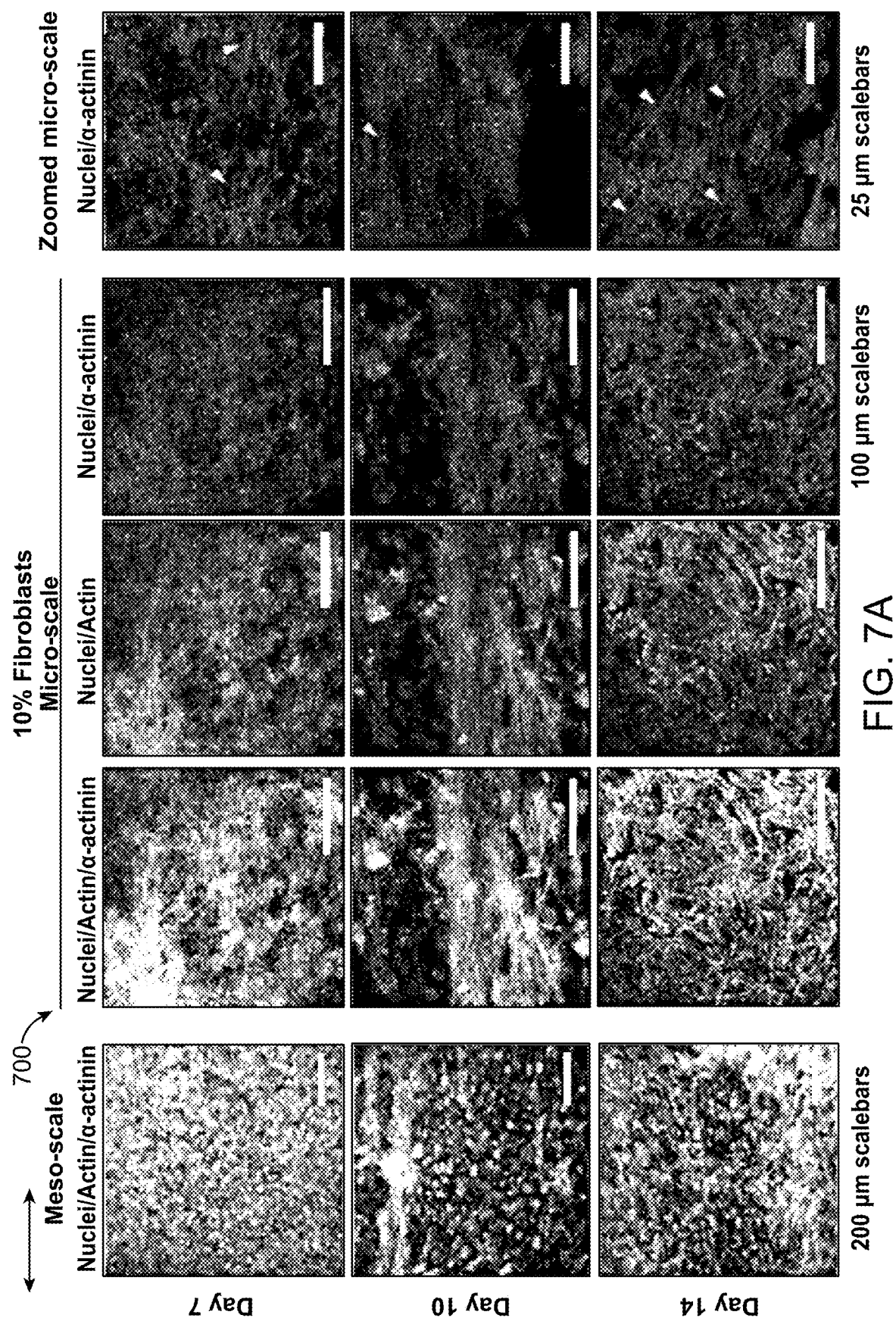
FIGS. 7A-7B show images of immunofluorescence staining of cardiac microtissues.
Figure 7B:
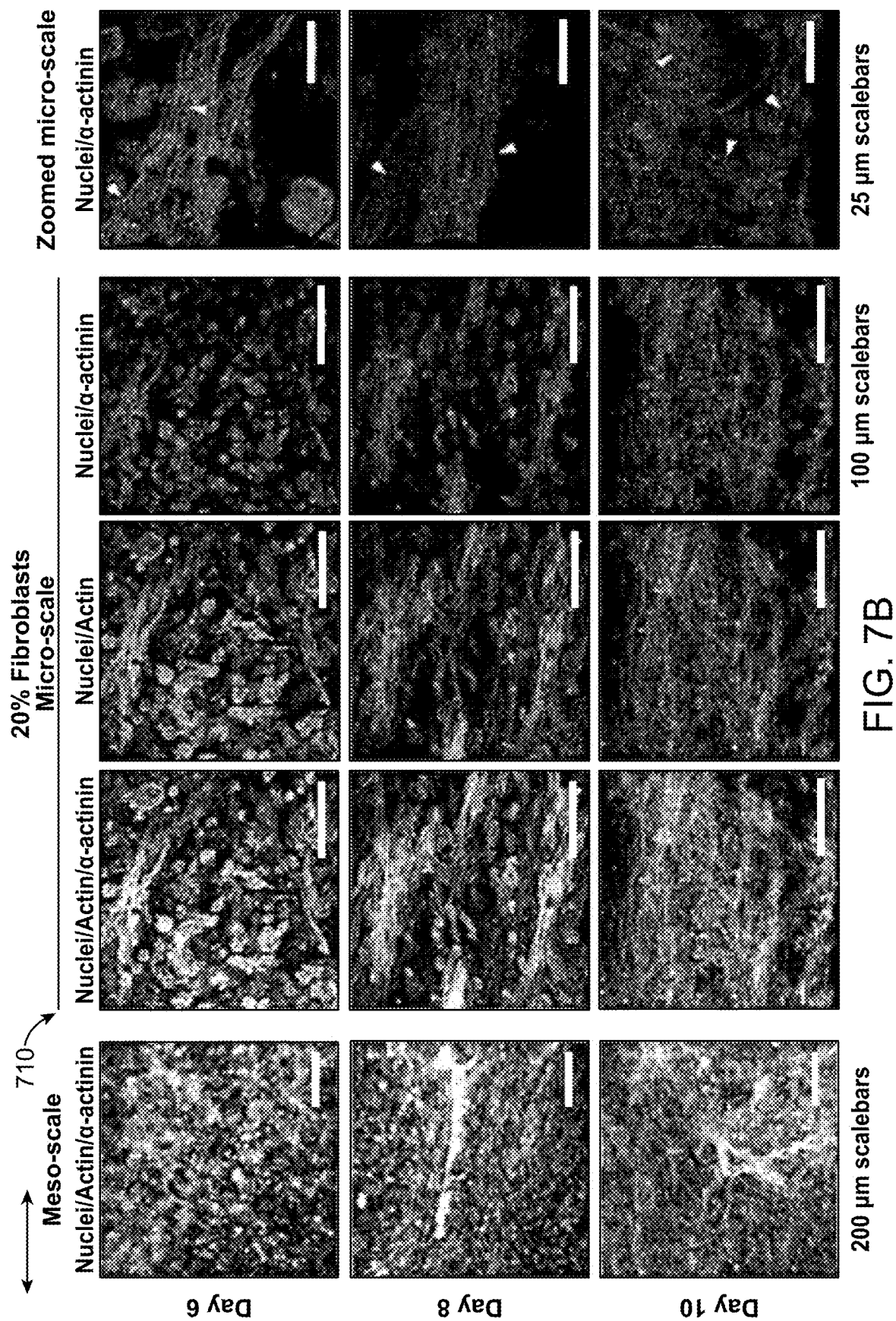
Figure 8A:
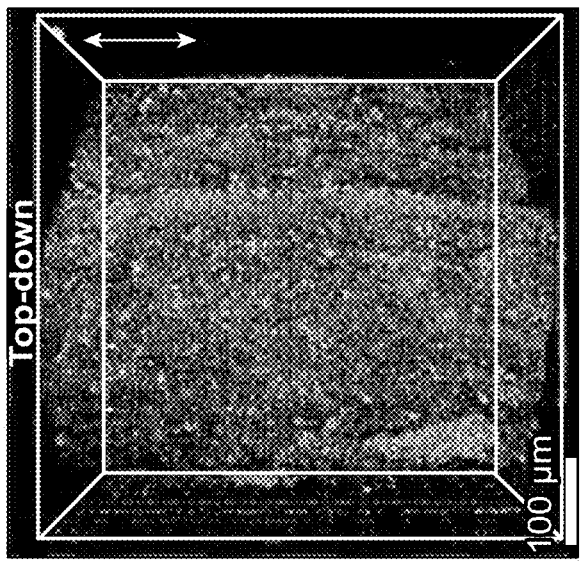
FIG. 8 shows tissue structure and cell organization.
Figure 8B:
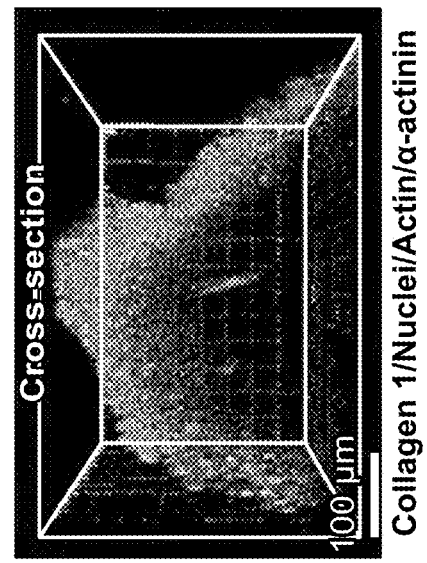
Figure 8C:
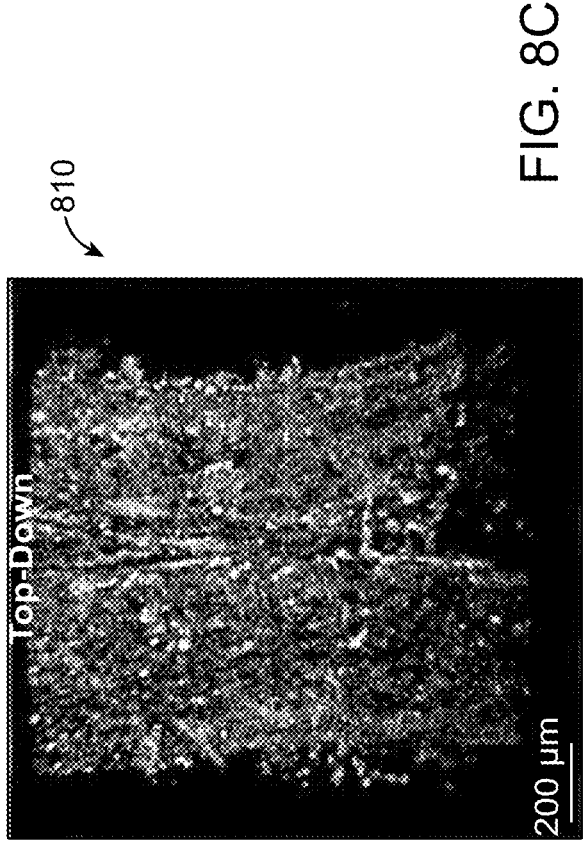
Figure 8D:
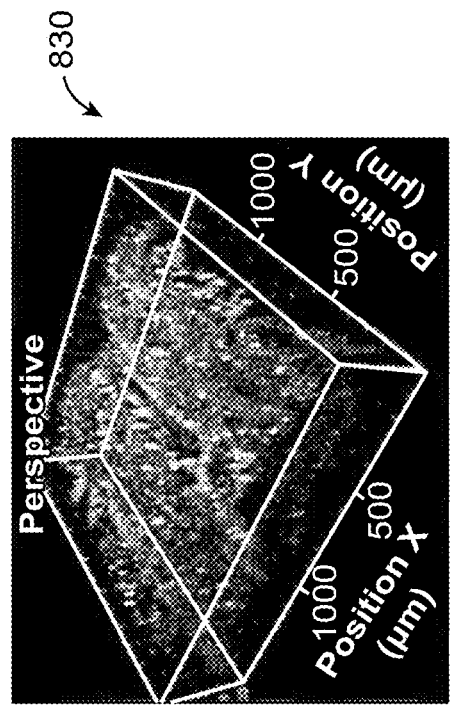

MIFI with 10% and 20% FBs were fixed and stained for sarcomeric α-actinin, F-actin, and nuclei to qualitatively observe if more spread, striated CMs were observed as length of culture time increased (FIG. 7A-7B). Generally, 10% FB MIFIs appeared to have more spread cells at all time points compared to 20% FB MIFIs, as observed by F-actin staining across samples. Additionally, 10% FB MIFIs did not appear to be out-populated by the FB sub-population of cells, as most tissues had cells with well-spread regions of α-actinin throughout, and striations were observed in these CMs as early as 7 days in culture. Tissues appeared to have sarcomeres that were more aligned in the direction of the long-axis of the MIFI as culture time was extended to 14 days. 20% FB MIFIs appeared to have less CM coverage until Day 10 of culture, but in these samples, sarcomeres did not appear to organize along the long-axis of the MIFIs as much as was observed in 10% FB MIFIs.

FIG. 7A shows meso-scale images 700 of CM tissues with 10% FBs stained for nuclei, actin, and sarcomeric α-actinin and that appear to show increased cell spreading as tissues were kept in culture over longer periods of time. Representative microscale images of features of the same tissues show that cells appear well spread for all time points, but the differences observed in meso-scale and microscale images at Day 10 compared to Day 7 and Day 14 may result from remodeling within tissues since visible beating was observed in wells beginning around Day 7. Sarcomeric α-actinin staining overlaps with most actin staining, showing that FBs are not overpopulating the tissues and CMs were the major cell type at all time points. Finally, zooming in on the microscale images shows striations are present in all of the μtissues, and they appear to became more organized and uniform over time (light arrows). Dark arrows represent a long axis of the tissues.

FIG. 7B shows meso-scale images of CM MIFIs with 20% FBs stained for nuclei, actin, and sarcomeric α-actinin appear to show increased cell spreading as tissues are kept in culture over longer periods of time. Representative microscale images of features of the same tissues show that cells were not as well spread at days 6 and 8 for 20% FB tissues compared to 10% FB tissues at Day 7. Sarcomeric α-actinin staining did not appear as dense at Day 6 and Day 8 tissues compared to Day 7, 10% FB tissues. However, zooming in on the microscale images showed striations were present in all of these tissues as well (light arrows). Dark arrows represent long axis of tissues.

Turning to FIG. 8 collagen I structure and cell organization are shown. Image 800 is a top down image of second-harmonic signal of Col I in fixed tissue with 10% FBs after 10 days in culture shows some alignment in the direction of the long axis of the tissue (represented by white arrows). Image 840 shows a cross-sectional view of Col I shows it is more densely packed in the outer 100 μm, likely due to cellular remodeling in this region. The cross section only shows half of the tissue; the Col and cells caused significant light scattering, and clearing methods will need to be used in the future to analyze full tissue cross-section and structure. Images 810, 830 show representative top down and perspective images of a day 10, 20% FB tissue stained for nuclei, actin, and α-actinin. A more densely packed middle region appears to be aligning parallel to the long axis of the tissue, resulting in a less elliptical tissue cross-section, a phenomenon observed in several of the 20% FB tissues.

The second-harmonic generation of Col I was used to observe the Col I structure in 10% FB MIFIs. The cells and Col I were densely packed in the outer 100 μm of MIFIs, so imaging the Col I structure past 400 μm will not be possible until clearing protocols are implemented to reduce light scattering and allow imaging through the full tissue thickness. Unsurprisingly, cells were generally restricted to the outer 100 μm of the MIFIs due to diffusion limits in these unvascularized tissues. Interestingly, in several of the 20% FB MIFIs at Day 10 of culture, the cells remodeled the middle region of the MIFI to be more compact and aligned with the long axis of the MIFI. It is possible that this less-uniform remodeling was also responsible for the breakage of 30-50% of MIFIS/trial that was observed in 20% FB samples.

Overall, striated CMs were found in the MIFIs after Day 6 for both 10% and 20% FB tissues. 10% FB MIFIs appeared to have better spread CMs at later time points and had more evenly distributed CMs at Days 7 and 10 compared to %20 FB MIFIs. Unsurprisingly, tissues had a 'dead zone' 100 μm deep into the tissues, likely because cells migrated to the outer region of the gel and began remodeling from the outside-in. However, more analysis needs to be done on cell-orientation, more precise cell-composition at different time points, and improved clearing or imaging methods must be implemented to further characterize these aspects of the engineered MIFIs.

FIG. 9 shows images 900, 910, 920 of finite element modeling of a bending PDMS strip 125 μm thick with the tissue modeled as connectors (dotted black lines) attached to either side of the strip. Images 900, 910, 920 represent strip bending under tissue loads of (A) 65 μN, (B) 75 μN, and (C) 85 μN, respectively. Plot 930 includes curves used to generate lookup tables from tissue length. Specifically, tissue length is plotted against and force required to bend the strip to said conformation, and each line represents a separate lookup table for strip thicknesses in 1 μm increments (125-150 μm and 154 μm).

Finite element modeling of bending of the thin, PDMS strips was used to generate lookup tables that relate tissue length and force required to induce bending of a strip to that conformation. Specifically, the strips were modeled as having connectors (or the tissue) attached at either side of the necking region of the strip shown in image 900. As the compressive force required to bend the strip increases, the connector (or tissue) length decreases, as shown in images 910, 920. In this way, plots of the relationship between tissue length and force exerted on PDMS strips were generated for strip thicknesses ranging from 125-154 μm, as shown in graph 930.

Figure 10:
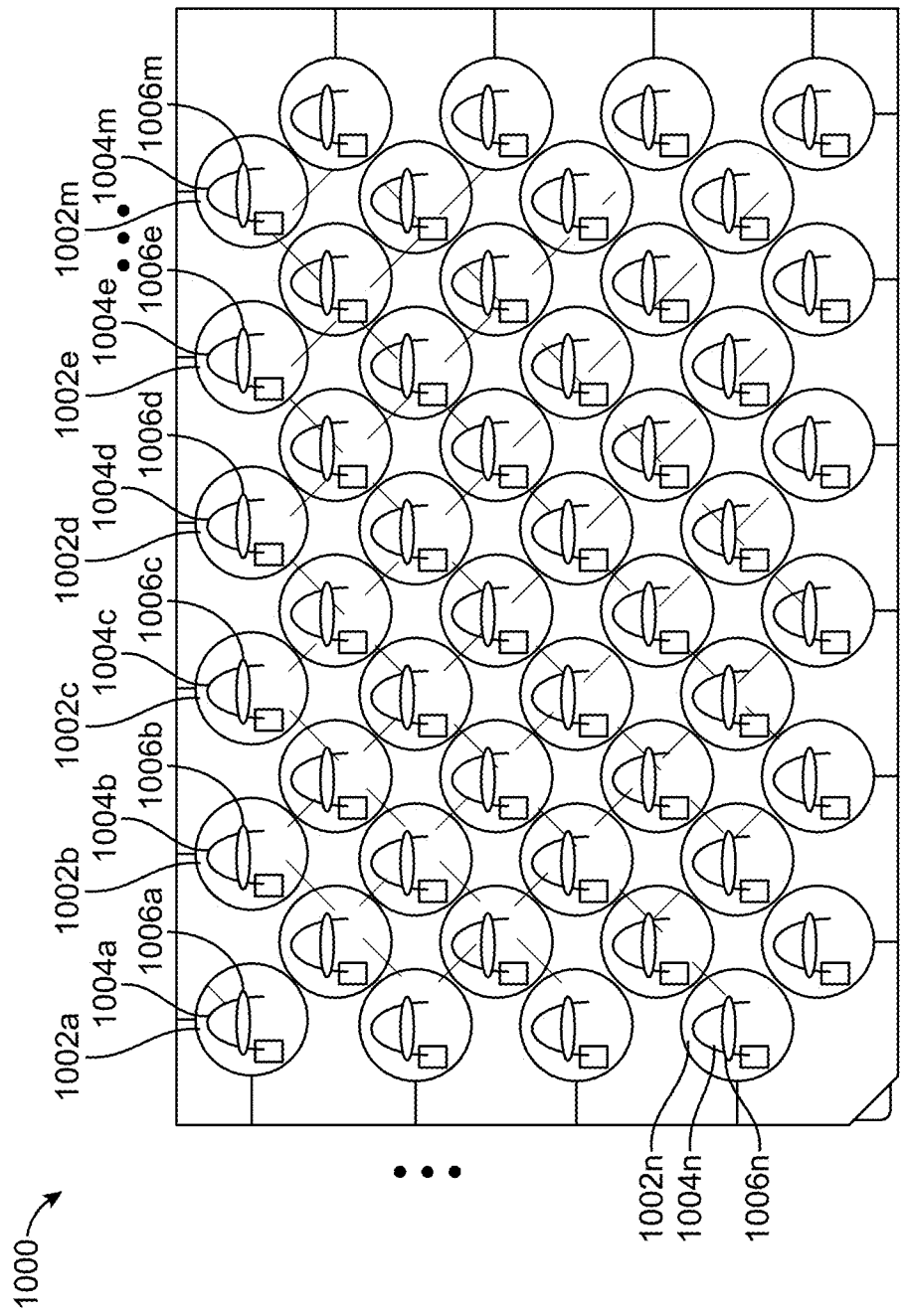
FIG. 10 shows an example well plate.

Turning to FIG. 10, a well plate 1000 is shown. The well plate can be used for high-throughput assays of tissue samples. Each well 1002 of the well plate 1000 includes a tissue-strip configuration as described above (e.g., well 100, strip 112, and tissue 200 of FIGS. 1A-2B). For example, each well has a strip 1004 that exerts a stress on the tissue, the stress being tuned to a particular value based on adjusting one or more parameters (e.g., length, width, thickness, elastic modulus, shape, etc.) of the strip. Each of strips 1004 can be tuned with pre-defined parameter values. The well plate 1000 can be configured to test a multitude of permutations of tissue compositions with different stresses on those tissues 1006. The well plate 1000 can form an N×M array of tissue samples, with N rows and M columns. In some implementations, each row or column (or both) can include strips 1004 with particular parameters that are identical to one another, and different tissue compositions, densities, etc. can be tested. In such a setup, each tissue sample 1006a-n and/or 1006a-m can be combined with a compound (e.g., a drug compound) to test the effects of the drug on the tissue 1004a-m. In some implementations, each well 1002a-m can include a unique combination of tissue composition and/or strip 1004 parameters. The strips 1004a-m and/or the tissues 1006a-m thus form a parameter space, including a parameter space of stress values by the strip (e.g., as a result of adjusting parameters of the strip), and/or a parameter space of tissues (e.g., by adjusting tissue composition, density, etc.), and/or a parameter space of compounds (e.g., drug compounds) being tested on the tissues 1004.

For example, each tissue 1004a-m can be injected with a compound, and the results measured for the respective tissue 1004a-m. The results measured can be based on the assay performed, and can include any of the effects mentioned herein, such as twitch force, contraction percentage, contractile force, etc. For example, the tissues can be introduced to any drug compound, including caffeine, isoprenaline, ephedrine, amphetamine, etc. In some implementations, a muscarinic agonist can be introduced (e.g., carbachol, pilocarpine, oxotremorine, etc.). The wells 1002a-m, strips 1004a-m, and tissues 1006a-m of well plate 1000 are thus useful for drug screening methods, because they provide a highly tunable tissue (particularly regarding contractile variability) that exhibits adult-like physiology.

Figure 11:
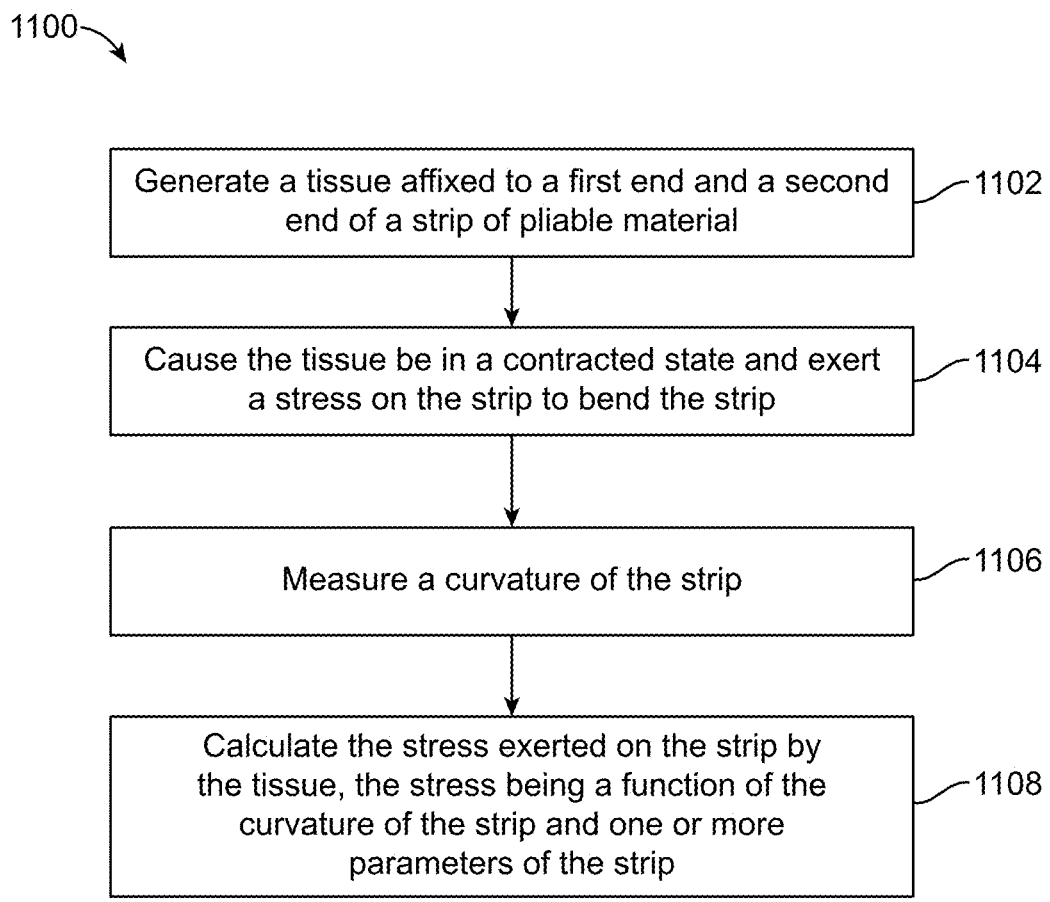
FIG. 11 shows a process for determining the contractile force of a tissue in a non-invasive manner.

FIG. 11 shows a process 1100 for performing a non-invasive contractility assay of a tissue (e.g., tissue 200 of FIGS. 2A-2B). The method includes generating (1102) a tissue that is affixed to a strip of bendable material. The tissue is affixed to a first end and a second, opposite end of the strip as described above. The method includes causing (1104) the tissue be in a contracted state and exert a stress on the strip to bend the strip. The tissue exerts a contraction force on the strip as described in relation to FIGS. 2A-2B. Here, causing the tissue to exert a stress force on the strip includes generating the tissue such that the tissue connects the first and second ends of the strip and causes the strip to bend. In addition to the contractile force of the tissue, additional contraction forces can be induced by stimulating the tissue with electrical signals. When the tissue is contracting (either in response to the electrical stimulation or when the tissue is removed from the well), the curvature of the strip is measured (1106). The curvature can be measured by image processing or other such techniques, as described in relation to FIG. 20. Measuring the curvature can include measuring an area under the curve of the strip, or other metrics for measuring the curvature can be used. The method includes calculating (1108) the stress exerted on the strip by the tissue, the stress being a function of the curvature of the strip and one or more parameters of the strip, the one or more parameters each having a value that is pre-determined. The stress is a function of the curvature of the strip and the known quantities of the thickness, material type, elastic modulus, width, length, shape, etc. of the strip. For example, for a known curvature of the strip, the stress that the strip is exerting on the tissue can be calculated. From the calculated stress of the strip on the tissue, the responsive contractility of the tissue can be determined.

Figure 12:
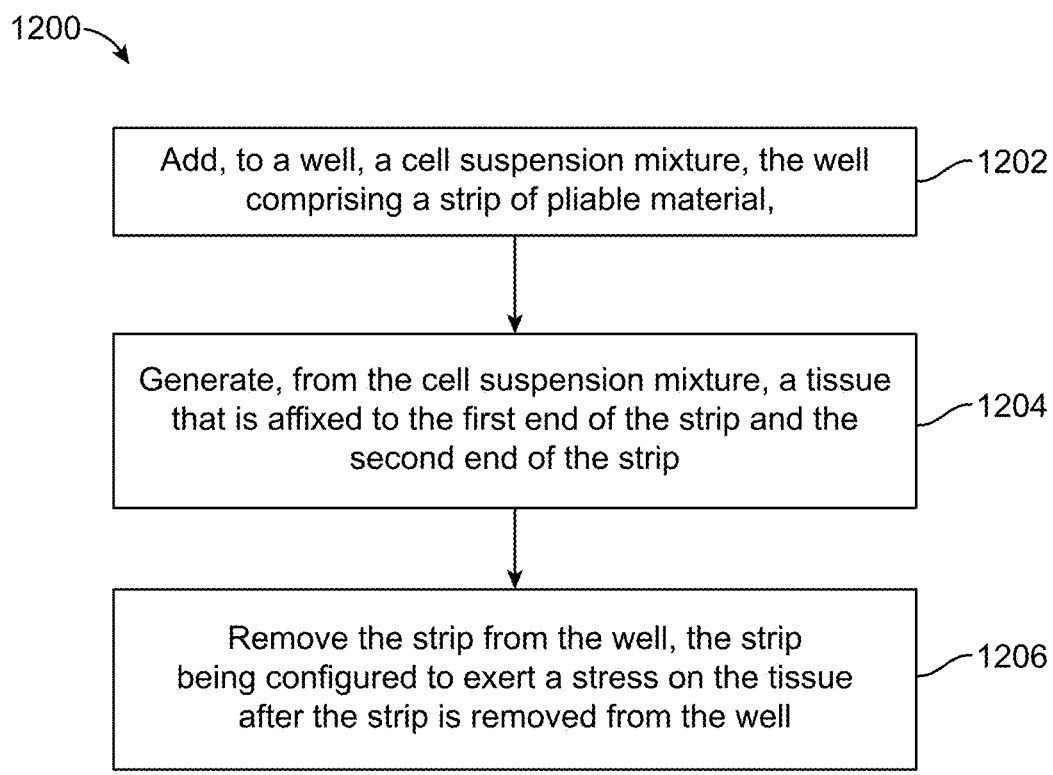
FIG. 12 shows a process for generating the tissue.

FIG. 12 shows a process 1200 for generating a generating a three dimensional tissue with an integrated load. The process 1200 includes adding (1202), to a well (e.g., well 100 of FIG. 1, 1002a-m of FIG. 10, etc.), a cell suspension mixture, the well comprising a strip of bendable material, wherein the strip of bendable material is inserted into the well at a first end and at a second end opposite the first end so that the strip is curved (e.g., as seen in FIGS. 1A-1B). The process 1200 includes generating (1204), from the cell suspension mixture, a tissue that is affixed to the first end of the strip and the second end of the strip. The process 1200 includes removing (1206) the strip from the well, wherein the strip is configured to exert a stress on the tissue after the strip is removed from the well, and wherein the strip exerts a reduced stress on the tissue before the strip is removed from the well relative to an increased stress on the tissue after the strip is removed from the well. The strip is configured to exert a reduced (e.g., non-maximum) amount of stress on the tissue before the tissue is removed from the well. In some implementations, the strip exhibits minimal/negligible stress on the tissue before the strip and tissue are removed from the well. The strip is configured to exert a maximum (e.g., unimpeded) stress on the tissue after the strip and tissue are removed from the well because the strip is no longer braced by the well.

Figure 13A:
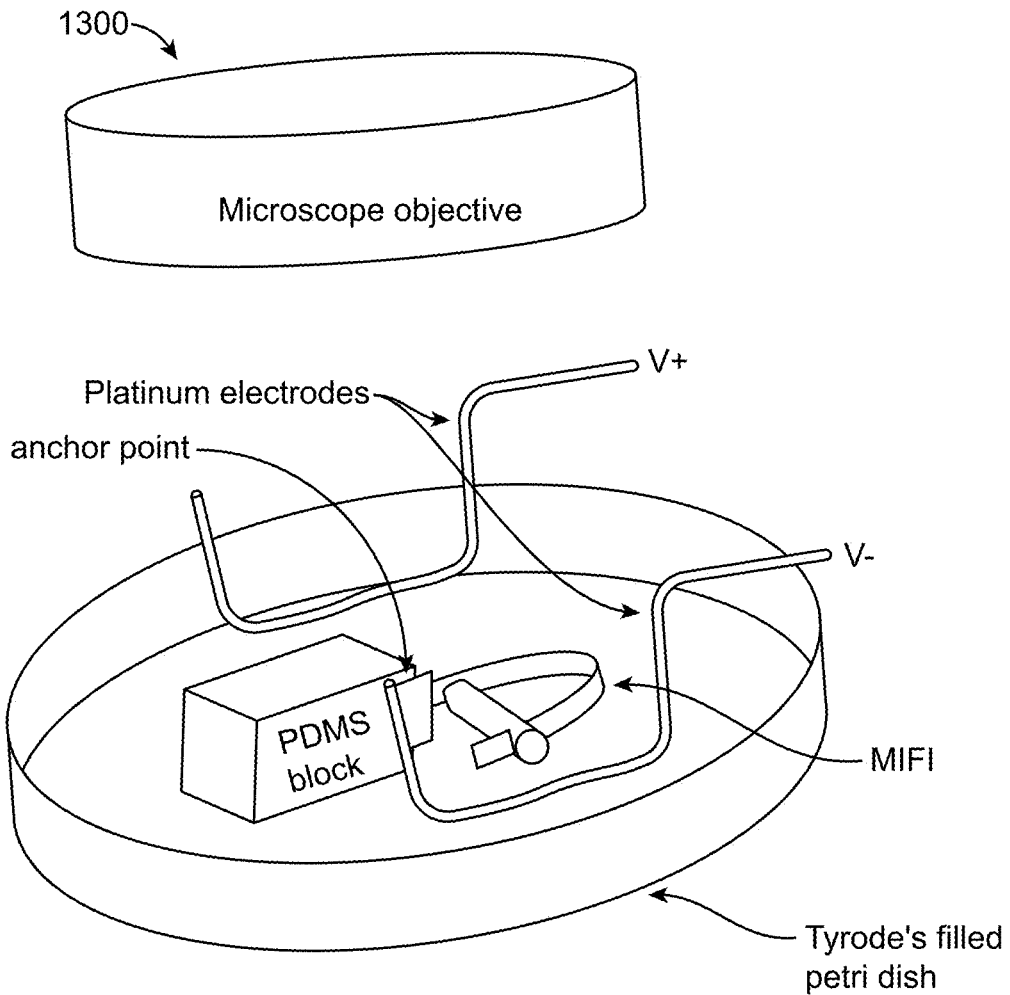
FIG. 13 shows a contractility assay system for determining the contractile force of a tissue in a non-invasive manner.
Figures 13B, 13C:
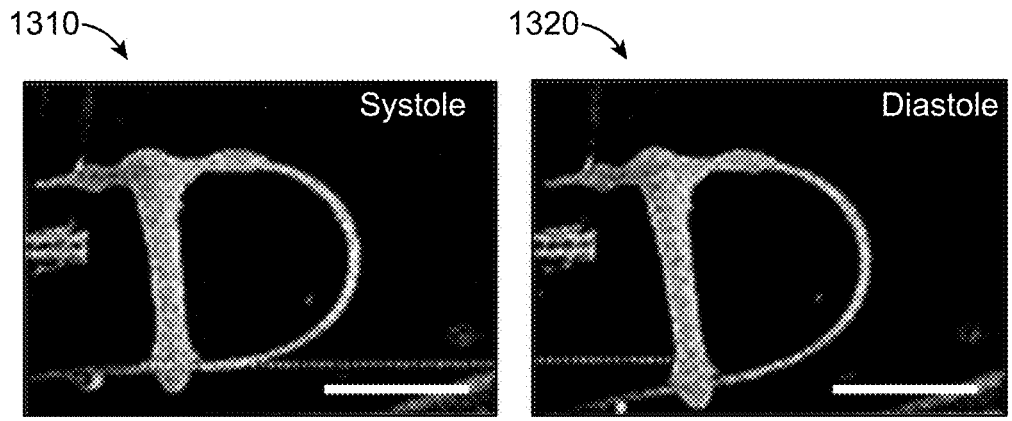

Turning to FIG. 13, a schematic 1300 shows a configuration of a side-on contractility assay for MIFIs. MIFIs were removed from wells for the contractility assay at Day 7, 10, or 14 (10% FBs) or at Day 6, 8, or 10 (20% FBs). By tracking the change in tissue length of beating MIFIs, we calculated force generated by these tissues using force lookup tables. MIFIs were removed from wells, one side of the strip was placed in a slit in a PDMS block to anchor the MIFI for side-on viewing, and the construct was submerged in Tyrode's and placed between two parallel platinum electrodes for later stimulation by assay device 1300. MIFIs spontaneously beat, resulting in visible deformation of the PDMS strip when imaged in the side-on contractility assay. Day 14, 10% FB MIFIs exerted significantly higher twitch force (3.62±1.7 µN) compared to 20% FB tissues at Days 6, 8 and 10 (1.03±0.70 µN, 1.65±1.4 µN, and 0.82±0.45 µN respectively). These tissues also beat with higher twitch force than Day 10 MIFIs with the same FB percentage (0:773±0.55 µN), shown in graph 1400 of FIG. 14. Day 7 MIFIs with 10% FBs also exerted higher twitch forces (2.44±1.3 µNT) than Day 10 MIFIs with 10% or 20% FBs. It is possible that this decrease in contractility at Day 10 was a result of remodeling in these tissues around Day 10, something that was reflected in the fluorescence staining. Because MIFIs began visibly beating in the wells by Day 7, it is possible that this induced the CMs and FBs to remodel the surrounding matrix at a mesoscopic level.

Tissues also responded to electric field stimulation and were capable of being electrically paced. When twitch forces of MIFIs paced at 2 Hz were measured, Day 14, 10% FB MIFIs exerted higher twitch force (3.07±1.54 µN) compared to Day 6, 8, and 10 MIFIs with 20% FBs (1.08±0.52 µN, 1.61±0.89 µN, and 0.93±0.426 µN). It appeared that, overall, 20% FB MIFIs did not exert as much force as 10% FB MIFIs. In part, this is due to earlier testing dates of the 20% tissues because these tissues were not able to be stably maintained in culture as long as the tissues with 10% FBs. Thus, these MIFIs had less time to mature and reorganize matrix, and the FBs in these tissues overpopulated the MIFIs and prevented, CMs from synchronizing throughout the tissue. Constructs at all time points were assessed for spontaneous beat frequencies which ranged from 60 BPM±15 (10% FB, Day 7) to 107 BPM±38 (20% FB, Day 10). However, no significant differences were found between groups since MIFIs at these time points native beat frequencies are still variable, something that had been observed in individual wells of differentiating CMs as well.

As stated above, FIG. 13 shows a schematic 1300 of the side-on contractility assay for MIFIs. The microscope objective views the top of the set up. The MIFI is placed on its side, with one strip anchored in a slit in a PDMS block glued to the bottom of the petri dish. The rvrIFI is submerged in Tyrodels and placed between two parallel platinum electrodes for electrical pacing. Side on images of cardiac MIFIs in the contractility assay image 1310 systole and image 1320 diastole, with the yellow dotted line showing the change in tissue length. Scale bars are 4 mm.

In FIG. 14 graph 1400 represents twitch forces (systole-diastole) for spontaneously beating tissues and shows that 10% PB tissues at Day 14 had significantly higher twitch forces than Day 10 samples with 10% FB and 20% PB samples at all time points. Day 7, 10% FB tissues also had significantly higher spontaneous twitch force than Day 10 samples with 10% or 20% FBs. Graph 1410 shows twitch forces for electrically paced (2 Hz) samples which showed similar trends, with Day 14, 10% FBs exerting significantly higher twitch force than Day 10, 10% and 20% FBs and Day 6, 20% FB samples. Twitch force appears to decrease slightly upon electrical stimulation, but variation in resulting forces decreases. Graph 1420 shows spontaneous beat frequencies (in BPM) of cardiac tissues with 10% or 20% FBs analyzed at Day 7, 10, 14 or Day 6, 8, and 10 in culture, respectively. No statistically significant differences were found among samples with n less than or equal to 3, with mean values ranging from 60 to 107 BPM (Day 7, 10% FBs and Day 10, 20% FBs, respectively).

Turning to FIG. 15, example force vs. time plots are shown of a Day 14, 10% FB MIFIs demonstrate a regular beat frequency and the ability to electrically pace the samples at 2 Hz 1500a. Titrating in isoprenaline, an excitatory drug, had the intended stimulatory effect on the native beat frequency of MIFIs at 500 nM and 5 µM shown in graphs 1500*b*,1500*c*, but it did not interrupt the ability to electrically pace the constructs at these concentrations. The addition of isoprenaline did not noticeably affect the twitch force of this specific MIFI at these concentrations, which exerted twitch forces ~4.6 µN when beating spontaneously in Tyrode's and ~4.0 µN when beating spontaneously in 5 M isoprenaline. Washing out the isoprenaline dosage with Tyrode's recovers the MIFI to its initial beat frequency, shown in graph 1500*d*. Subsequent treatment with 55 mM caffeine also increased the spontaneous beat frequency with minimal impact on the twitch force, and dosing with the muscarinic agonist, carbachol, reduced the spontaneous beat frequency while having surprisingly little impact on twitch force, as shown in graphs 1500*e-f*.

While most MIFIs beat more synchronously as culture time increased, occasionally disease-like arrhythmic beating was observed in these Day 14 construct, seen in image 1500*g*. While this disease-like construct was still able to be electrically paced, its native and paced beating plots of force reflect the abnormal beating, especially when compared to more synchronous constructs such as shown in graph 1500*a*. To determine if the MIFI could recover to a more normal beating phenotype, increasing carbachol doses were administered (500 nM, 5 µM, and 50 µM) and resulted in improvement in the spontaneous beat frequency of the constructs, but the twitch force profiles were still ~30% the strength of the twitch force of synchronous constructs, shown in graph 1500*h*. The arrhythmic construct was electrically paced at doses of 5 µM and 50 µM of carbachol. Unlike electrical stimulation of the construct with no drug treatment graph 1500*g*, the combinatorial effect of carbachol treatment with electric pacing at 2 Hz resulted in significantly higher twitch forces and a normal phenotype beating waveform was observe, such as shown in graph 1500*i*. More interestingly, a significant interaction between the stimulation and drug treatment was found during 2-way ANOVA analysis of twitch force under these conditions shown in graph 1600 of FIG. 16. 2-Hz pacing significantly increased twitch force with or without drug treatment, and pacing coupled with 5 or 50 µM carbachol resulted in 2.5× and 2.8× stronger twitch contraction, in graph 1600.

Turning to FIG. 16, additional analysis of specific specimens of Day 14, 10% FB MIFIs showed decreasing twitch force as stimulatory drug dose was increased. Specifically, one MIFI exerted 3.54 µN±0.12 spontaneous twitch force and 3.34±0.935 twitch force under 2 Hz pacing with no drug treatment, shown in chart 1610. Dosing with 500 nM isoprenaline resulted in a drop to ~80% of initial twitch force to 2.85 µN±0.84 and 2.81 µN±0.71 for spontaneous and 2 Hz paced beating, respectively. Increasing drug dosage to 5 mM resulted in an even further decrease (1.78 µM±0.21) to ~50% of initial twitch strength, and electric pacing at 2 Hz was unable to recover full twitch strength (2.15 µN±0.33). Epinephrine treatment of a separate MIFI construct also resulted in a dose-dependent decrease in twitch force, shown in graph 1620. Specifically, during spontaneous beating, no drug treatment and 500 nM drug treatment resulted in 5.93 µN±0.44 and 5.49 µN±0.25 twitch force respectively. These values dropped to 66% and 61% of the initial twitch force at 5 µM and 50 µM epinephrine doses. Interestingly, two-way ANOVA analysis found that, the effect of electrical stimulation was significantly higher only as dosage of epinephrine increased. The twitch forces at 5 µM and 50 µM were significantly recovered by electrical pacing back to 85% and 80% of initial twitch force, respectively. While it is not initially intuitive that some stimulatory drugs resulted in decreasing twitch force as dosage increased, it is possible that this was a result of increased beat frequency of the constructs, resulting in an increased diastolic force between beats. This hypothesis is also supported by the evidence that pacing constructs at 2 Hz significantly improved the twitch force of dosed constructs, shown in graphs 1600 and 1620.

The magnitude change in BPM was compared, and each MIFI was normalized to its native beat frequency due to the wide range of beat frequencies shown in all constructs. MIFIs dosed with increasing concentrations of isoprenaline beat at 1.2 1×±0.2, 1.27×±0.10, and 1.48×±0.47 initial beat frequency for 50 nM, 500 nM, and 50 µM treatments, respectively, shown in graph 1640. Epinephrine dosing similarly affected MIFI beating frequencies by raising it to 1.42×±0.51 and 1.65×±0.47 initial BPM, shown in chart 1650. Finally, caffeine dosing at 5 mM significantly increased BPM to 1.59×±0.451 initial BP, shown in chart 1630. Thus, a cardiac tissue was engineered by co-culturing HUES9-CMs and FBs and integrating a U-shaped PDMS strip, and MIFIs induced visible bending of the strip and responded as expected to pharmacological stimuli.

Figure 17:
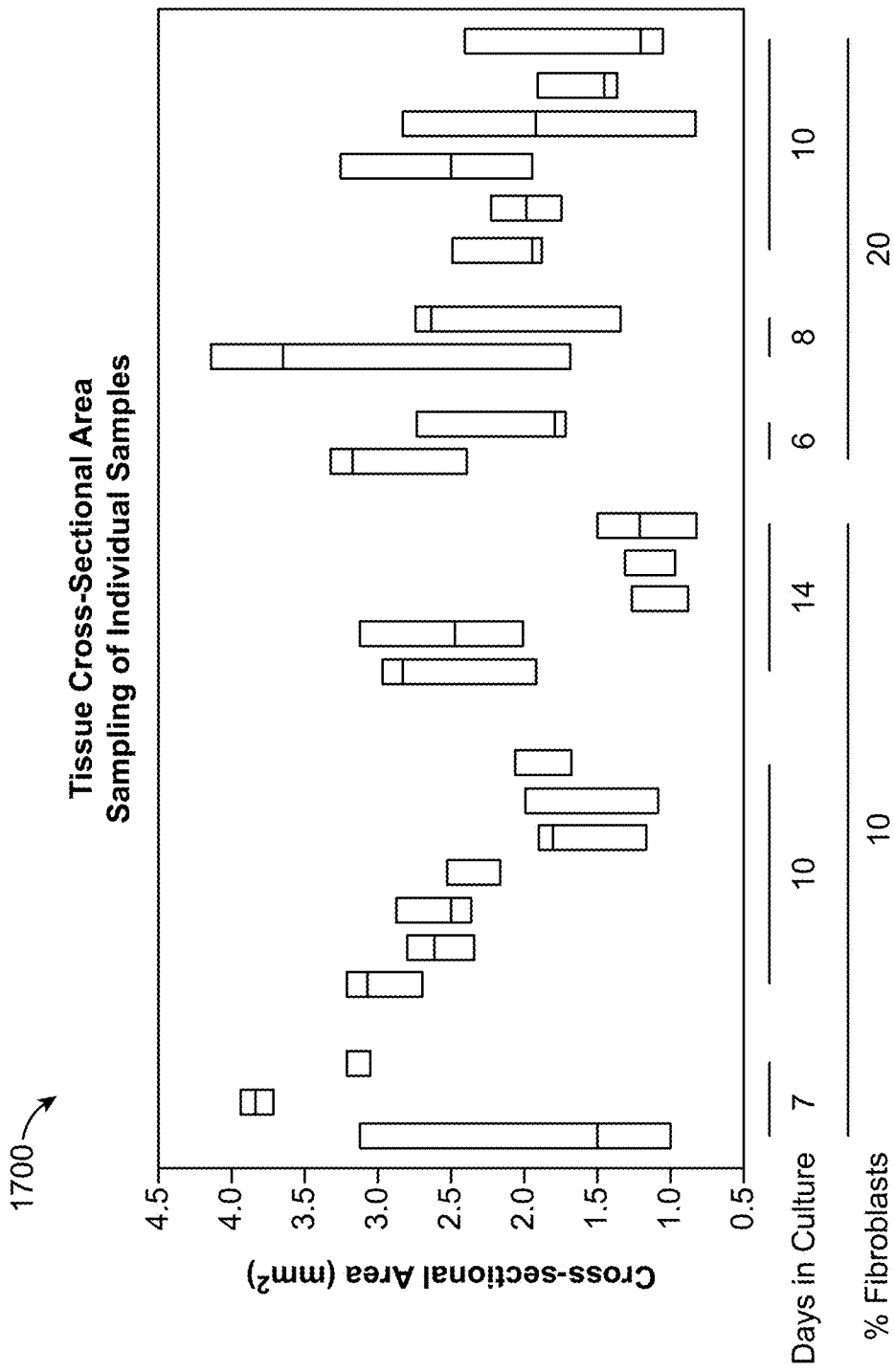
FIG. 17 shows measured cross-sectional areas of tissue samples.

Turning to graph 1700 of FIG. 17, a fuller characterization of MIFIs was made to calculate the force measurements per cross-sectional area of the full tissue section as well as the muscle-only cross-section, a step that is necessary to determine if the actual muscle cells in specific tissues are stronger at specific time points. Average tissue width and thickness were measured to approximate an ellipsoidal cross-section to perform initial normalization calculations. The ellipsoidal cross-section was measured by measuring 3 points per construct, and the distribution of calculated cross-sections had higher variability in the 20% FB constructs, which is reflective of the less-uniform compaction observed in those tissues.

Figure 18:
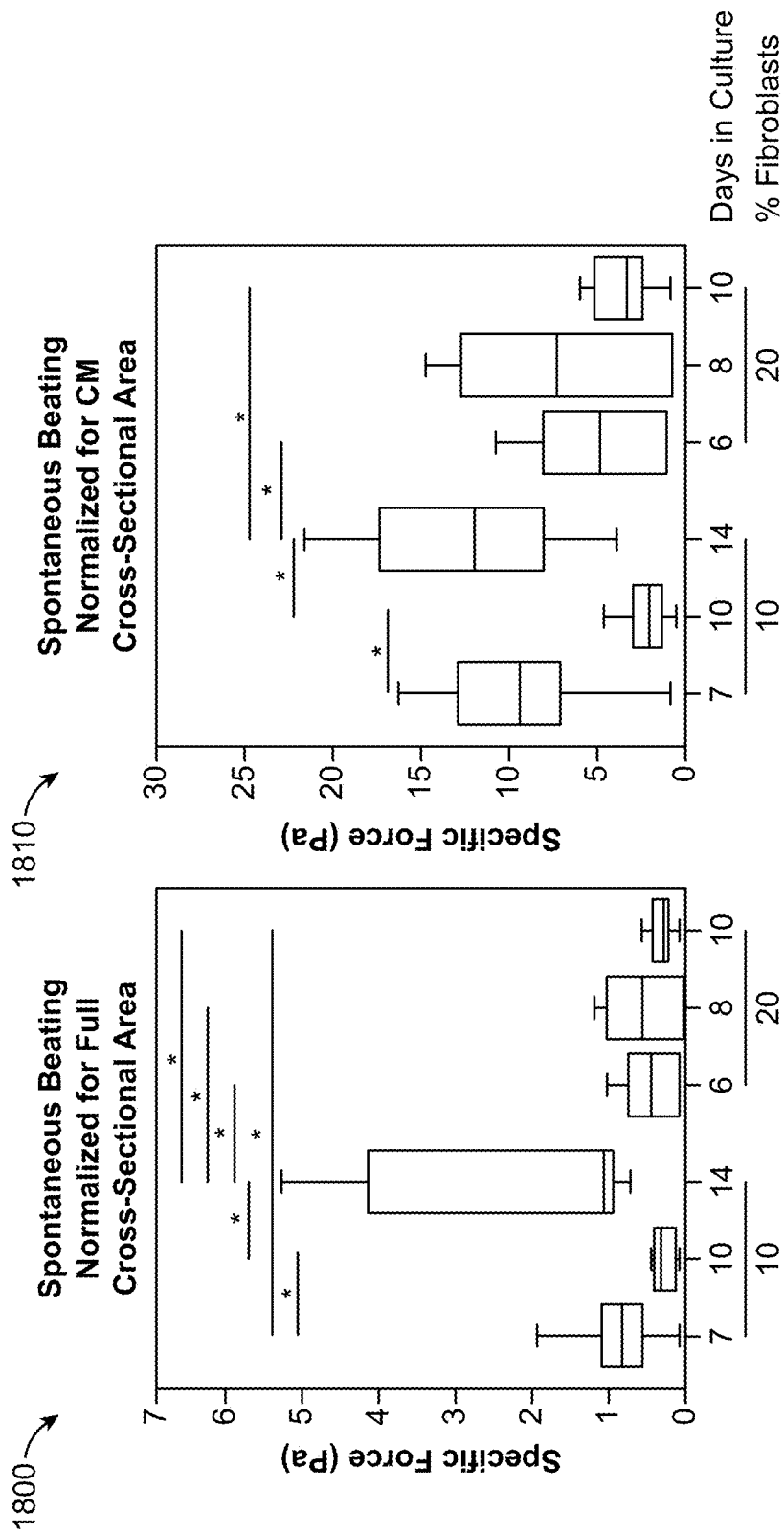
FIG. 18 shows measured twitch forces normalized for tissue cross-sectional area.
Figure 19:
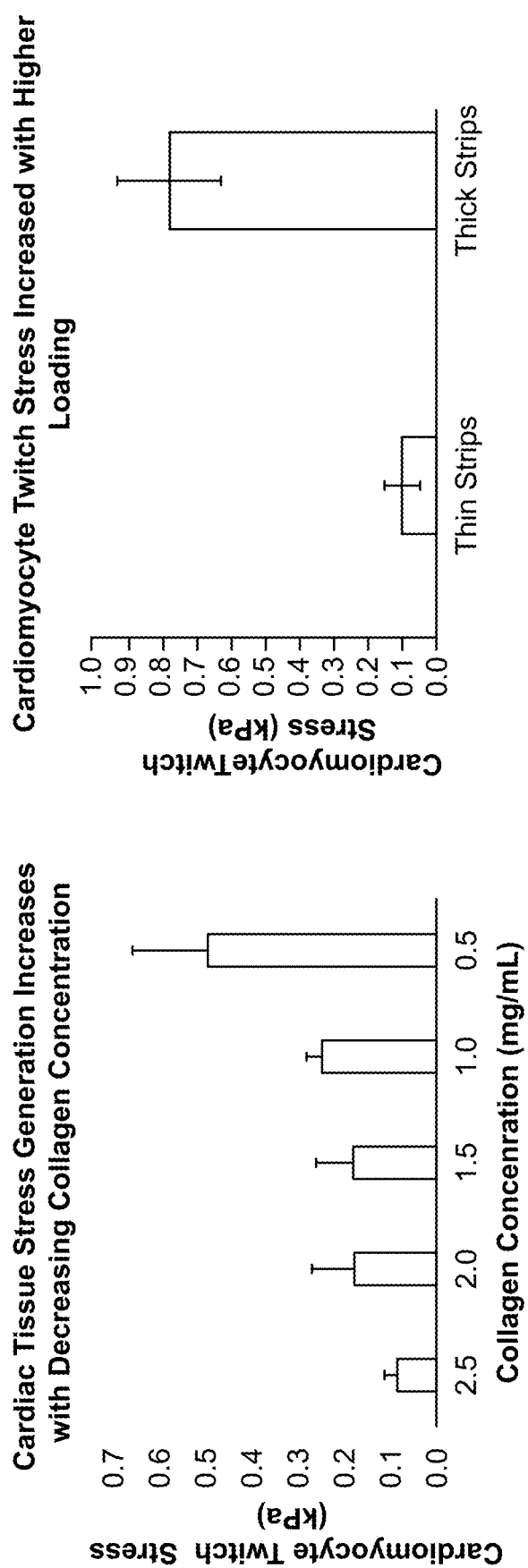
FIG. 19 shows stress generation of a tissue relative to concentration of collagen used to form the 3D tissue and to the thickness of the strip used to provide a mechanical loading to the tissues.

Turning to FIG. 18, graphs 1800, 1810 show that when each MIFI was normalized to its average ellipsoidal cross-section, D14, 10% FB MIFIs were found to exert higher specific force (med=1.1 Pa) compared to 20% FB MIFIs at D6 (med=0.45 Pa), D8 (med=0.56 Pa) and D10 (med=0.29 Pa) and compared to D10, 10% FB MIFIs (med=0.30 Pa). D7 10% FB MIFIs exerted higher specific twitch force (med=0.85 Pa) compared to D10 MIFTs for both 10% and 20% FB constructs. To further approximate the actual force per muscle cross-section, the outer 100 µm of MIFIs were assumed to contain cells, based on initial imaging and the diffusion limits of non-vascularized tissues. The outer, cell-containing region was estimated at composing of 90% CMs for 10% FB constructs and 80% CMs for 20% FB constructs to calculate the normalized force per muscle cross-section.

Using these approximations, D14 10% FB MIFIs was determined to exert significantly higher specific force per CM area (med=12.0 Pa) compared to D6 and D10 20% FB MIFIs (meds=4.8 Pa and 3.7 Pa, respectively) and compared to D10 10% FB MIFIs (med=1.9 Pa), shown in graph 1810. D7 10% FB MIFIs exerted higher forces per approximated muscle cross-section (med=9.4 Pa) than D10 10% FB constructs (shown in graph 1810). This dip in force at D10 for 10% FB constructs may have occurred because of tissue remodeling and cell reorganization that occurred after CMs began to visibly deform the strips in the wells after Day 7. More importantly, these approximations to normalize force for tissue cross-section and CM cross-section still exhibit that constructs are stronger by D14 of culture, and 10% FB constructs have more uniform remodeling compared to 20% FB constructs.

Figure 20:
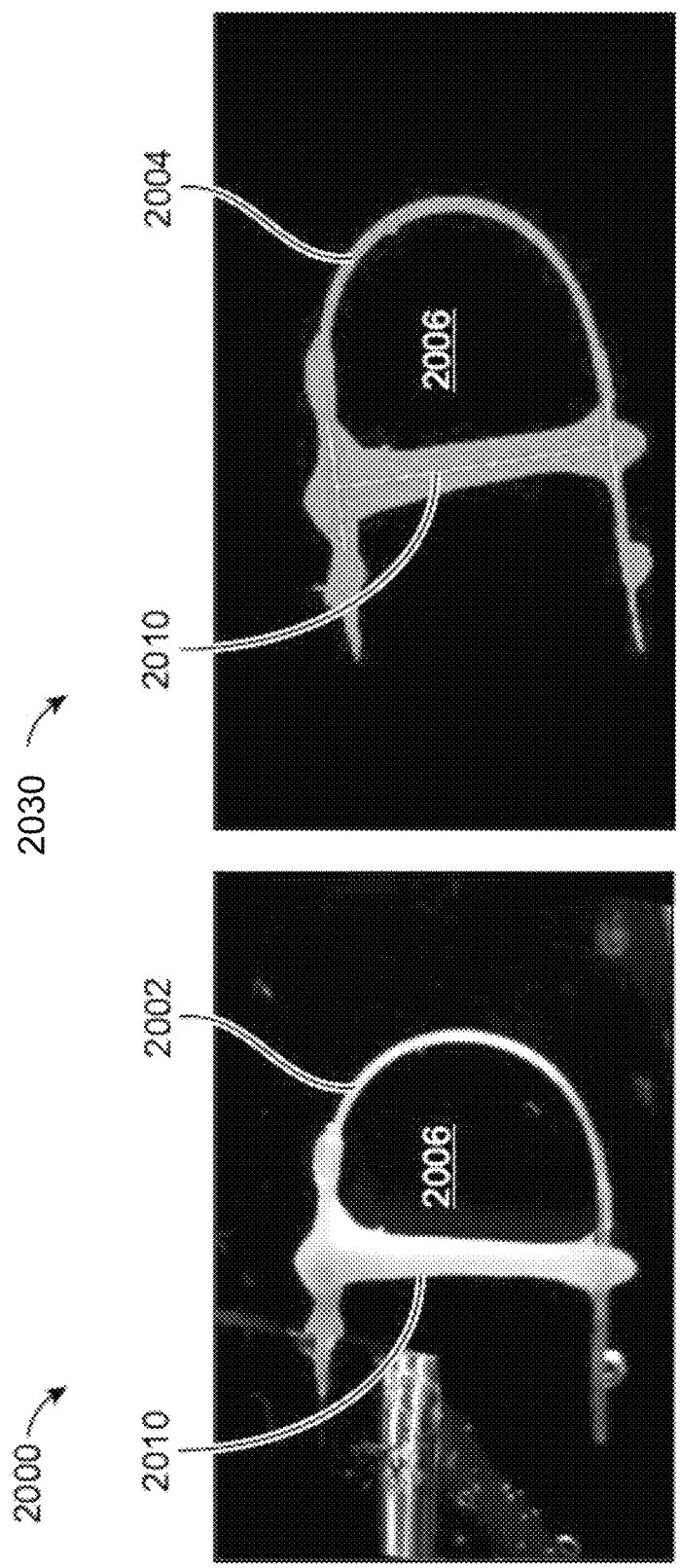
FIG. 20 shows images for determining stress generation of a tissue in a non-invasive manner where the tissue length, length of the strip between tissue attachment points and curvature of the strip are identified using an image analysis program.

FIG. 20 shows an example of image processing of an example tissue 2010. Image 2000 includes an unprocessed image of a strip 2002 (e.g., strip 112) affixed to a tissue 2010

(e.g., tissue 200). The strip 2002 exerts a load on tissue 2010. The tissue provides a contractile force that causes the strip 2002 to bend. The amount of force that the tissue 2010 is exerted is determined in a non-invasive manner by taking an image of the tissue (such as image 200) and determining the curvature of the strip 2002 in the image 2000. In some implementations, the area 2006 inside the tissue 2010 and the strip 2002 is measured to determine the curvature of the strip 2002. The image 2000 is image processed (e.g., by color thresholding, line extraction, etc.) to extract the tissue 2010 and the strip 2004 locations in the image. Image 2030 is an example of a processed image, where the features of the tissue 2010 and the strip 2004 have been extracted. Area 2006 is calculated and used to determine the curvature of the strip 2004. The curvature of the strip 2004 is used in combination with the known parameters of the strip (e.g., width, thickness, length, elastic modulus, shape, etc.) to determine what load or stress is being exerted on the tissue by the trip. The determined stress value is used to calculate the contractile force exerted by the tissue. The image 2000 can be taken when the tissue is static or when the tissue is being stimulated (e.g., by an electrical signal).

Various inventive features of a system for generating 3D tissues with integrated loading have been described above. It will be appreciated that not all inventive features need be combined in a single embodiment. Rather, some inventive features may be included within other embodiments without using other inventive features. It is to be understood, however, that even though numerous characteristics and advantages of the present tissue generation system have been set forth in the foregoing description, together with details of the structure and function of the tissue generation system, the disclosure is illustrative only, and changes may be made in detail, especially in matters of shape, size and arrangement of parts within the principles of the tissue generation system to the full extent indicated by the broad general meaning of the terms in which the appended claims are expressed.

What is claimed is:

1. A system for generating a tissue, the system comprising:
   a strip of bendable material, the strip comprising:
      a first region in proximity to a first end of the strip for coupling to a tissue comprising organic material; and
      a second region in proximity to a second end of the strip for coupling to the tissue, the second end being opposite the first end,
      wherein the strip is configured to bend to align the first region with the second region; and
   a well for generating the tissue, the well comprising:
      a region for generating the tissue from a cell culture;
      a first slit configured to receive the first end of the strip and expose the first region of the strip to the tissue generation region; and
      a second slit configured to receive the second end of the strip and expose the second region of the strip to the region of the well;
      wherein the first slit is aligned with the second slit to align the first region of the strip and the second region of the strip in the region to enable the tissue to couple to the first region of the strip and to couple to the second region of the strip during generation of the tissue; and
      wherein the strip is removable from the well.

2. The system of claim 1, wherein the well is configured to reduce a stress exerted by the strip on the tissue during generation of the tissue relative to a maximum stress that the strip is configured to exert on the tissue; and
   wherein the strip is configured to exert the maximum stress on the tissue when the strip and the tissue are removed from the well.

3. The system of claim 2, wherein the strip is configured to provide a stress of up to approximately 10,000 kPa on the tissue when the strip and the tissue are removed from the well.

4. The system of claim 2, wherein a magnitude of the stress exerted on the tissue by the strip is a function of one or more tuned parameters of the strip, the parameters comprising a length of the strip, a width of the strip, a thickness of the strip, an elastic modulus of the strip, and a shape of the strip.

5. The system of claim 1, wherein the tissue is configured for contracting between approximately 10%-40% of an initial length of the tissue.

6. The system of claim 1, wherein a cell suspension of the well comprises an approximate mixture of either 0.5 to 10 mg/mL Collagen Type I or fibrin, 20% gel matrix, 10% 10× phosphate buffered saline, and either $18.75 \times 10^6$ cells/mL for cardiomyocytes or $15 \times 10^6$ cells/mL for myoblasts.

7. The system of claim 1, wherein a cell suspension of the well comprises a concentration of between approximately $10\text{-}100 \times 10^6$ cells/mL and fibroblasts comprising approximately 10-20% of a total cell count.

8. The system of claim 7, wherein cells of the cell suspension comprise one of smooth muscle cells, skin cells, ligament cells, and tendon cells.

9. The system of claim 1, wherein the well is a part of a multi-well plate.

10. The system of claim 9, wherein at least one well of the multi-well plate corresponds to a respective strip having particular parameters, and wherein at least one strip and well of the multi-well plate represent a loading value of a parameter space representing loading values for the tissue.

11. The system of claim 10, wherein the particular parameters of the strip comprise an elastic modulus parameter, a thickness parameter, a width parameter, and a length parameter.

12. The system of claim 1, wherein the tissue comprises one of a cardiac tissue, skeletal tissue, smooth muscle tissue, skin tissue, cartilage, tendon, and ligament.

13. The system of claim 1, wherein the strip comprises one of polydimethylsiloxane (PDMS), polytetrafluoroethylene film, a polycarbonate film, or an elastomer film.

14. The system of claim 1, wherein each of the first region and the second region of the strip has a narrower width than a width of a portion of the strip between the first region and the second region.

15. The system of claim 1, wherein the tissue forms striations in response to a stress exerted on the tissue by the strip.

16. The system of claim 1, wherein cells within the tissue align in response to a stress exerted on the tissue by the strip.

17. The system of claim 1, wherein the tissue is configured to undergo a strain of up to 80% by the strip when the strip and tissue are removed from the well.

18. A method of generating a three dimensional tissue, the method comprising:
   adding to a well a cell suspension mixture, the well comprising a strip of bendable material, wherein the strip of bendable material is inserted into the well at a first end and at a second end opposite the first end so that the strip is curved;

generating, from the cell suspension mixture, a tissue that is affixed to the first end of the strip and the second end of the strip; and removing the strip from the well, wherein the strip is configured to exert a stress on the tissue after the strip is removed from the well, and wherein the strip exerts a reduced stress on the tissue before the strip is removed from the well relative to an increased stress on the tissue after the strip is removed from the well.

* * * * *

UNITED STATES PATENT AND TRADEMARK OFFICE
CERTIFICATE OF CORRECTION

| | | |
|---|---|---|
| PATENT NO. | : 11,926,844 B2 | Page 1 of 1 |
| APPLICATION NO. | : 16/638544 | |
| DATED | : March 12, 2024 | |
| INVENTOR(S) | : Adam Feinberg, Rebecca Duffy and Jacqueline Wittmer | |

It is certified that error appears in the above-identified patent and that said Letters Patent is hereby corrected as shown below:

On the Title Page

Column 1, item (22) PCT Filed: delete "Aug. 8, 2018" and insert -- Aug. 15, 2018 --

Signed and Sealed this
Seventh Day of May, 2024

Katherine Kelly Vidal
*Director of the United States Patent and Trademark Office*